(12) United States Patent
Mayaudon et al.

(10) Patent No.: US 8,871,434 B2
(45) Date of Patent: *Oct. 28, 2014

(54) RED BLOOD CELL STORAGE MEDIUM FOR EXTENDED STORAGE

(75) Inventors: Véronique Mayaudon, Gognies-Chaussée (FR); Jean-Marc Payrat, Nivelles (BE)

(73) Assignee: Fenwal, Inc., Lake Zurich, IL (US)

( * ) Notice: Subject to any disclaimer, the term of this patent is extended or adjusted under 35 U.S.C. 154(b) by 848 days.

This patent is subject to a terminal disclaimer.

(21) Appl. No.: 12/408,483

(22) Filed: Mar. 20, 2009

(65) Prior Publication Data

US 2009/0239208 A1 Sep. 24, 2009

Related U.S. Application Data

(60) Provisional application No. 61/038,536, filed on Mar. 21, 2008, provisional application No. 61/096,534, filed on Sep. 12, 2008.

(51) Int. Cl.
- *A01N 1/02* (2006.01)
- *A61M 37/00* (2006.01)
- *A61K 35/18* (2006.01)

(52) U.S. Cl.
CPC .. *A01N 1/02* (2013.01); *A61K 35/18* (2013.01)
USPC ............................................. 435/2; 604/6.02

(58) Field of Classification Search
None
See application file for complete search history.

(56) References Cited

U.S. PATENT DOCUMENTS

| | | | |
|---|---|---|---|
| 4,267,269 A | 5/1981 | Grode et al. | |
| 4,356,172 A | 10/1982 | Nakao et al. | |
| 4,572,899 A | 2/1986 | Walker et al. | |
| 4,585,735 A * | 4/1986 | Meryman et al. | 435/2 |
| 4,880,786 A | 11/1989 | Sasakawa et al. | |
| 4,961,928 A | 10/1990 | Holme et al. | |
| 4,980,277 A | 12/1990 | Junnila et al. | |
| 5,147,776 A | 9/1992 | Koerner, Jr. | |
| 5,248,506 A | 9/1993 | Holme et al. | |
| 5,250,303 A | 10/1993 | Meryman et al. | |
| 5,288,605 A | 2/1994 | Lin et al. | |
| 5,364,756 A | 11/1994 | Livesey et al. | |
| 5,387,187 A | 2/1995 | Fell et al. | |
| 5,405,742 A | 4/1995 | Taylor | |
| 5,439,882 A | 8/1995 | Feola et al. | |
| 5,445,629 A * | 8/1995 | Debrauwere et al. | 604/403 |

(Continued)

FOREIGN PATENT DOCUMENTS

| | | |
|---|---|---|
| DE | 4002693 | 3/1991 |
| EP | 0044864 | 8/1981 |

(Continued)

OTHER PUBLICATIONS

Bohmer et al., The effect of stress upon hydrolysis adenine nucleotides in blood serum of rats, Pharmacology, Biochemistry and Behavior, (2003), vol. 75, pp. 467-471.*

(Continued)

*Primary Examiner* — Alexander Kim
(74) *Attorney, Agent, or Firm* — Cook Alex Ltd.

(57) ABSTRACT

Synthetic aqueous storage solutions are disclosed for use in the processing and the storing of red blood cells prepared from whole blood including cells derived from whole blood held for an extended period at room temperature.

18 Claims, 20 Drawing Sheets

(56) References Cited

U.S. PATENT DOCUMENTS

| | | | |
|---|---|---|---|
| 5,446,030 A | 8/1995 | Weisz et al. | |
| 5,459,030 A | 10/1995 | Lin et al. | |
| 5,480,773 A | 1/1996 | Ogata et al. | |
| 5,494,590 A | 2/1996 | Smith | |
| 5,496,821 A | 3/1996 | Arduino | |
| 5,554,527 A | 9/1996 | Fickenscher | |
| 5,601,972 A | 2/1997 | Meryman | |
| 5,624,794 A | 4/1997 | Bitensky et al. | |
| 5,629,145 A | 5/1997 | Meryman | |
| 5,674,741 A | 10/1997 | Watanabe et al. | |
| 5,769,839 A | 6/1998 | Carmen et al. | |
| 5,783,093 A | 7/1998 | Holme | |
| 5,789,151 A | 8/1998 | Bitensky et al. | |
| 5,827,643 A | 10/1998 | Conrad et al. | |
| 5,840,252 A | 11/1998 | Giertych | |
| 5,888,824 A | 3/1999 | Isogawa et al. | |
| 5,899,874 A | 5/1999 | Jonsson | |
| 5,906,915 A * | 5/1999 | Payrat et al. | 435/2 |
| 5,908,742 A | 6/1999 | Lin | |
| 6,039,711 A | 3/2000 | Headley et al. | |
| 6,068,970 A | 5/2000 | Hosono et al. | |
| 6,150,085 A | 11/2000 | Hess et al. | |
| 6,251,580 B1 | 6/2001 | Lin et al. | |
| 6,277,556 B1 | 8/2001 | Grode et al. | |
| 6,348,156 B1 | 2/2002 | Vishnoi et al. | |
| 6,440,372 B1 | 8/2002 | Pages | |
| 6,447,987 B1 | 9/2002 | Hess et al. | |
| 6,527,957 B1 | 3/2003 | Deniega et al. | |
| 6,548,241 B1 | 4/2003 | McBurney et al. | |
| 6,566,046 B2 | 5/2003 | Lin et al. | |
| 6,579,672 B1 | 6/2003 | Granger et al. | |
| 6,652,475 B1 | 11/2003 | Sahines et al. | |
| 6,811,778 B2 | 11/2004 | Page et al. | |
| 6,857,191 B2 | 2/2005 | Whited | |
| 6,866,992 B2 | 3/2005 | Lin et al. | |
| 6,936,413 B1 | 8/2005 | Bischof et al. | |
| 7,011,761 B2 | 3/2006 | Muller | |
| 7,087,177 B2 | 8/2006 | Min et al. | |
| 7,156,240 B2 | 1/2007 | Oishi et al. | |
| 7,264,608 B2 | 9/2007 | Bischof et al. | |
| 7,267,817 B2 | 9/2007 | Page et al. | |
| 7,297,272 B2 | 11/2007 | Min et al. | |
| 7,332,125 B2 | 2/2008 | Cianci et al. | |
| 7,531,098 B2 | 5/2009 | Robinson et al. | |
| 2001/0049089 A1 | 12/2001 | Dottori et al. | |
| 2002/0131958 A1 | 9/2002 | Chapman et al. | |
| 2002/0146400 A1 | 10/2002 | Cincotta | |
| 2002/0164795 A1 | 11/2002 | Gen | |
| 2002/0177116 A1 | 11/2002 | Wiggins et al. | |
| 2003/0113704 A1 | 6/2003 | Stassinopoulos | |
| 2003/0124504 A1 | 7/2003 | Bitensky et al. | |
| 2003/0148256 A1* | 8/2003 | Payrat et al. | 435/2 |
| 2003/0153074 A1 | 8/2003 | Bitensky et al. | |
| 2004/0029096 A1 | 2/2004 | Steen | |
| 2004/0043374 A1 | 3/2004 | DePablo et al. | |
| 2004/0106094 A1 | 6/2004 | Payrat et al. | |
| 2004/0132207 A1 | 7/2004 | Arima et al. | |
| 2004/0137417 A1 | 7/2004 | Ryan | |
| 2005/0031596 A1 | 2/2005 | Crowe et al. | |
| 2005/0053516 A1 | 3/2005 | Whitaker et al. | |
| 2005/0064381 A1 | 3/2005 | Lucas et al. | |
| 2005/0074743 A1 | 4/2005 | Purmal et al. | |
| 2005/0137516 A1 | 6/2005 | Min et al. | |
| 2005/0137517 A1 | 6/2005 | Blickham et al. | |
| 2005/0208462 A1 | 9/2005 | Bitensky et al. | |
| 2005/0233302 A1 | 10/2005 | Hess et al. | |
| 2005/0256443 A1 | 11/2005 | Bischof et al. | |
| 2005/0277108 A1 | 12/2005 | Bitensky et al. | |
| 2006/0127375 A1 | 6/2006 | Livesey | |
| 2006/0226090 A1 | 10/2006 | Robinson et al. | |
| 2006/0275271 A1 | 12/2006 | Chow | |
| 2006/0292544 A1 | 12/2006 | Hassanein et al. | |
| 2007/0020607 A1* | 1/2007 | Meryman et al. | 435/2 |
| 2007/0048726 A1 | 3/2007 | Baust et al. | |
| 2007/0105220 A1 | 5/2007 | Crowe et al. | |
| 2007/0178168 A1 | 8/2007 | Ho et al. | |
| 2007/0178434 A1 | 8/2007 | Natan et al. | |
| 2007/0190636 A1 | 8/2007 | Hassanein et al. | |
| 2007/0298406 A1 | 12/2007 | Pena et al. | |
| 2008/0050275 A1 | 2/2008 | Bischof et al. | |
| 2008/0176209 A1 | 7/2008 | Muller et al. | |
| 2008/0233554 A1 | 9/2008 | Sehgal et al. | |
| 2011/0117647 A1 | 5/2011 | Mayaudon et al. | |

FOREIGN PATENT DOCUMENTS

| | | |
|---|---|---|
| EP | 0301250 A1 | 1/1989 |
| EP | 0367271 A1 | 9/1990 |
| WO | WO8803027 A1 | 5/1988 |
| WO | WO9214360 A1 | 9/1992 |
| WO | WO9416099 A1 | 7/1994 |
| WO | WO96029864 A1 | 10/1996 |
| WO | WO9716967 A1 | 5/1997 |
| WO | WO0223988 A1 | 3/2002 |
| WO | WO2004105483 A1 | 12/2004 |
| WO | WO2006088455 A1 | 8/2006 |
| WO | WO2007054160 A2 | 5/2007 |
| WO | WO2007082916 A1 | 7/2007 |
| WO | WO2008037481 A2 | 4/2008 |
| WO | WO2008089337 A1 | 7/2008 |
| WO | WO2008107724 A2 | 9/2008 |
| WO | WO2008113017 A2 | 9/2008 |

OTHER PUBLICATIONS

Graefe et al., Sensitive and Specific Photometric Determination of Mannitol in Human Serum, Clin Chem Lab Med., (2003), vol. 41, pp. 1049-1055.*

Jacobs et al., Determination of Citric Acid in Serum and Urine Using Br82, Journal of Nuclear Medicine, (1964), vol. 5, pp. 297-301.*

Blood WebMD, last viewed on Nov. 15, 2011.*

Test-blood MedlinePlus, last viewed on Nov. 15, 2011.*

Common Laboratory (LAB) Values; last viewed on Nov. 15, 2011.*

Hess et al., An update on solutions for red cell storage., Vox sanguinis, (2006), vol. 91, pp. 13-19.*

Pietersz et al. Platelet Concentrates Stored in Plasma for 72 Hours at 22° C. Prepared from Buffycoats of Citrate-Phosphate-Dextrose Blood Collected in a Quadruple-Bag Saline-Adenine-Glucose-Mannitol System, Vox Sang., (1985), vol. 49, pp. 81-85.*

Strauss et al., Preservation of red blood cells with purines and nucleosides. II. Uptake and utilization of purines and nucleosides by stored red blood cells. Folia Haematol Int Mag Klin Morphol Blutforsch. (1980) vol. 107(3), pp. 434-453.*

Hess et al., Alkaline CPD and the preservation of RBC 2,3-DPG, Transfusion, (2002), vol. 42, Issue 6, pp. 747-752.*

D. Mazor, A. Dvilansky and N. Meyerstein; Prolonged Storage of Red Cells: The Effect of pH, Adenine and Phosphate; Vox Sang 1994; 66:264-269; Hemotology Service and the Dr. Joseph Kaufmann Hemotology Laboratory, Ben Gurion University of the Negev, Beer-Sheva, Israel.

John R. Hess, Neeta Rugg; Jenny K. Gormas, Amy D. Knapp, Heather R. Hill, Cynthia K. Oliver, Lloyd E. Lippert, Edward B. Silberstein and Tibor J. Greenwalt; RBC Storage for 11 Weeks; Transfusion 1586-1590; vol. 41, Dec. 2001; Blood Components XP009115151.

John R. Hess, Heather R. Hill, Cynthia K. Oliver; Lloyd E. Lippert and Tibor J. Greenwalt; Alkaline CPD and the Preservation of RBC 2,3-DPG; Transfuson Jun. 2002;42:747-752; vol. 42, Blood Components XP007911813.

E. Beutler and W. Kuhl; Volume Control of Erythrocytes During Storage, The Role of Mannitol; pp. 353-357; XP-000909765; Department of Basic and Clinical Research, Research Institute of Scripps Clinic, LaJolla, California, (1988).

European Search Report and Annex, Feb. 26, 2010; pp. 1-3; Munich, Germany.

Hogman et al., "Clinical usefullness of red cells preserved in protein-poor mediums", New England Journal of Medicine, 1978, vol. 229 (25), pp. 1377-1382.

(56) References Cited

OTHER PUBLICATIONS

Hogman et al., "Storage of whole blood before separation: the effect of temperature on red cell 2, 3 DPG and the accumulation of lactate", Transfusion, 1999, vol. 39 (5) pp. 492-497.

Hess et al.,"Alkaline CPD and the preservation of RCB 2,3-DPG", Transfusion, 2002, vol. 42, pp. 747-752.

Hogman et al., Sep. 2006, Storage of Red Blood Cells with Improved Maintenance of 2, 3 Biphosphoglycerate, Transfusion, vol. 46, pp. 1543-1552.

Heaton, 1992, Evaluation of Posttransfusion Recovery and Survival of Transfused Red Cells, Transfusion Medicine Reviews, vol. 6, pp. 153-169.

Hess et al, 2002, Storage of Red Blood Cells; New Approaches, Transfusion Medicine Reviews, vol. 16, pp. 283-295.

Hogman et al., 2002, Improved Maintenance of 2,3-DPG and ATP in RBCs Stored in a Modified Additive Solution, Transfusion, vol. 42, pp. 824-829.

Tinmouth et al., 2001, The Clinical Consequences of the Red Cell Storage Lesion, Transfusion Medicine Reviews, vol. 15, pp. 91-107.

Hogman et al., 1999, Storage Parameters Affecting Red Blood Cell Survival and Function After Transfusion, Transfusion Medicine Reviews, vol. 13, pp. 275-296.

Hess et al., The Effect of Two Additive Solutions on the Posthaw Storage of RBCs, Transfusion, Jul. 2001, pp. 923-927, vol. 41.

Hess et al., Twelve-week RBC Storage, Transfusion, Jul. 2003, pp. 867-872, vol. 43.

Extended European Search Report and Office Action received from the European Patent Office for EP Application No. 09004074.2 dated Mar. 5, 2010.

Notice of Transmittal of International Search Report & Written Opinion received from the International Searching Authority for PCT/US10/50036 dated Jan. 21, 2011.

EP Communication dated May 29, 2012 for EP Application No. 12000538 with European Search Report and Annex dated May 21, 2012.

\* cited by examiner

STORAGE DAY - HOLDING 8 HOURS

—□— E-Sol 2
—△— SAG-M

STORAGE DAY - HOLDING 12 HOURS

STORAGE DAY - HOLDING 8 HOURS

—□— E-Sol 2
—△— SAG-M

STORAGE DAY - HOLDING 12 HOURS

Figure 5C
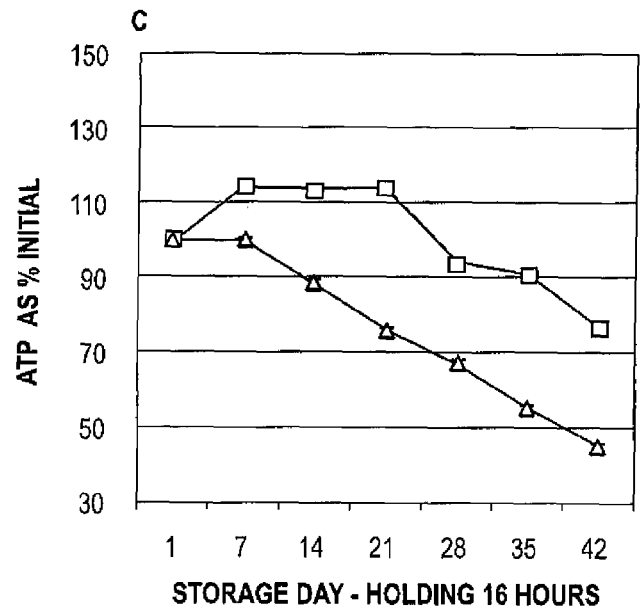
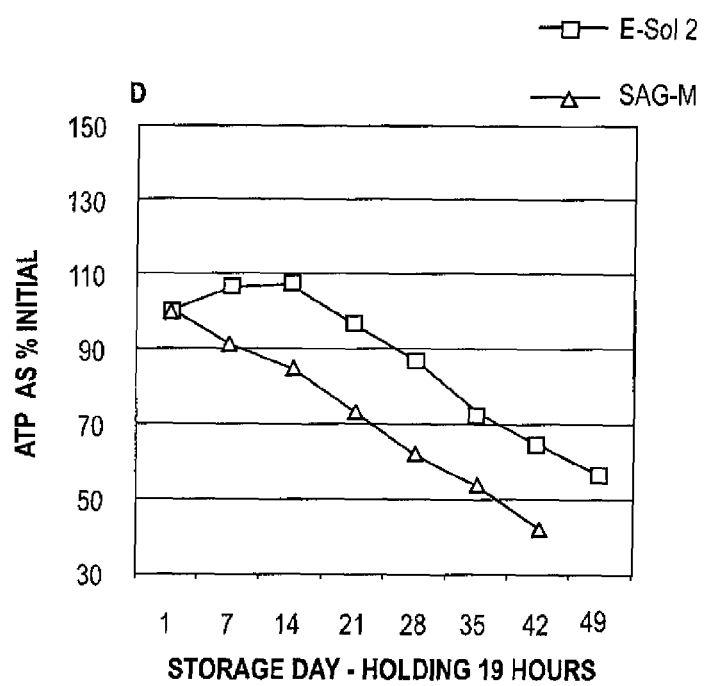
Figure 5D

Day Holding HT:16h

SAG-M
E-Sol 2

HT:19h

RED BLOOD CELL STORAGE MEDIUM FOR EXTENDED STORAGE

REFERENCE TO OTHER APPLICATIONS

This patent application claims the benefit of U.S. Provisional Patent Application Ser. No. 61/038,536, filed Mar. 21, 2008, and U.S. Provisional Patent Application Ser. No. 61/096,534 filed Sep. 12, 2008, both of which are incorporated by reference in their entirety.

FIELD OF THE DISCLOSURE

The present disclosure relates to storage solutions for blood components such as red blood cells. More particularly, the present disclosure relates to storage solutions that allow red blood cells to preserve functionality for an extended period of time such as, but not limited to, at least 35 days in storage even when the red blood cells are prepared from whole blood that is held for at least several hours prior to processing.

DESCRIPTION OF RELATED ART

Methods of preparing red blood cells from whole blood as well as methods of storing red blood cells for later transfusion to a patient are well known. Various synthetic solutions useful for the storage of red blood cells are disclosed, for example, in U.S. Pat. No. 5,250,303 (Meryman), U.S. Pat. No. 5,906,915 (Payrat et al.) and U.S. Pat. No. 6,150,085 (Hess et al.) which are incorporated herein by reference in their entirety. Other storage solutions for red blood cells include Adsol, SAG and SAG-M which are respectively disclosed in U.S. Pat. No. 4,267,269, Högman et al., New England Journal of Medicine, Dec. 21, 1978; 229 (25); 1377-82 and European Published Patent No. 0044 864, the disclosures of which are incorporated herein by reference in their entirety. For example, Högman et al. (above) describe a storage solution (SAG) containing (in 100 mls), 877 mg of sodium chloride, 16.9 mg of adenine, and 900 mg of glucose which may be added to packed red blood cells prepared from one unit of blood to increase the storage life of the red blood cells. European Published Patent No. 0 044 864 discloses SAG-M in which the concentration of glucose (or fructose) is increased and mannitol is added to a conventional SAG solution.

BACKGROUND

Whole blood is made up of various cellular components such as red cells, white cells and platelets suspended in its liquid component, plasma. Whole blood can be separated into its constituent components (cellular or liquid), and the separated component can be administered to a patient in need of that particular component. For example, red blood cells may be separated from the whole blood of a healthy donor, collected, and later administered to a patient.

Commonly, more than one component of blood is prepared from a unit of whole blood. For instance, red blood cells, plasma and platelets may all be prepared from the same unit of whole blood. Protocols used to prepare blood components often involve the addition of an anticoagulant containing citrate such as, but not limited to, citrate phosphate dextrose (CPD) to the collected whole blood. However, the optimal protocol for the preparation and storage of one component may often differ from the protocol for the preparation and storage of another component. For instance, units of whole blood used to prepare platelets are typically stored at room temperature, approximately 20-24° C., often approximately 22° C., before processing, while storage at approximately 4° C. is optimal for the preparation of red blood cells.

At blood processing centers or similar locations, it is often convenient to accumulate a large number of units of whole blood before separating (i.e., processing) the blood components. The processing of multiple units of blood at one time, for example, in the morning of the day following collection reduces processing costs and also ensures uniformity of preparations. For example, staff for processing the blood may be required only during business hours (rather than requiring staff to work after business hours to process blood collected that same day) and a consistent routine may be readily developed. However, whole blood may be held for at least 8 hours and up to 26 hours before processing and separation of blood components when this procedure is followed.

While holding blood overnight provides logistical and staffing benefits to the blood center, the holding of blood for 8 or more hours is not without its drawbacks when it comes to preserving or maintaining the functionality of certain components, such as red blood cells. For example, compared to samples in which whole blood was held for only 8 hours or less at room temperature before the preparation of red blood cells, holding whole blood at room temperature overnight, which is at least 8 hours and may be up to 26 hours, generally is associated with the reduction of 2, 3-DPG (2,3-diphosphoglycerate) to very low levels, an initial increase in ATP levels followed by a steady decline during storage at 4° C., and reduced levels of extracellular potassium when the cells are stored in a red cell storage solution. Even within the 8-hour range, rapid cooling of whole blood to room temperature is recommended if the hold temperature will be beyond 4 hours to avoid initial loss of 2,3-DPG. (Högman et al., Transfusion. 1999; 39 (5):492-497). These effects of holding of whole blood before processing may be a consequence of an association between the rate of synthesis of 2,3-DPG and the intracellular pH of red blood cells where breakdown of 2,3-DPG is favored below pH 7.2. (Hess et al., Transfusion 2002; 42: 747-752.)

In addition, compared to storage at cooler temperatures, the increased metabolism of red blood cells stored at room temperature results in increased production of lactic acid (and also at temperatures above room temperature) resulting in a rapid fall to lower pH levels. While storage of whole blood at 4° C. and the consequent reduction of red blood cell metabolic rate may delay this effect, platelets, on the other hand, cannot be prepared from blood stored at 4° C.

Consequently, the preparation of red blood cells and platelets from the same unit of whole blood that has been held at room temperature until processing may impair the functionality of the red blood cells and reduce the time that the red blood cells may be stored. Therefore, it would be desirable to provide a storage solution that allows the long term storage of red blood cells prepared from whole blood that has been held at room temperature (20-24° C.) for extended periods of time before processing.

SUMMARY

In one aspect, the present disclosure is directed to an aqueous storage solution for red blood cells that includes about 1 mM to about 2.2 mM adenine, about 20 mM to about 110 mM mannitol, about 2.2 mM to about 90 mM sodium citrate, about 16 mM to about 30 mM sodium phosphate dibasic, and about 20 mM to about 70 mM glucose where the pH of the aqueous storage solution is above about 8.0.

In another aspect, the present disclosure is directed to a red blood cell composition that includes an amount of red blood cells; and an aqueous storage solution, where the aqueous storage solution includes about 1 mM to about 2.2 mM adenine, about 20 mM to about 110 mM mannitol, about 2.2 mM to about 90 mM sodium citrate, about 16 mM to about 30 mM sodium phosphate dibasic, and about 20 mM to about 70 mM glucose, where the pH of the aqueous storage solution is above about 8.0

In another aspect, the present disclosure is directed to methods for storing red blood cells including providing a unit of anticoagulated whole blood, holding the whole blood from about four hours to about twenty-six hours; separating the red blood cells from the whole blood; and adding to the separated red blood cells an aqueous storage solution wherein the aqueous storage solution includes 1 mM to about 2.2 mM adenine, about 20 mM to about 110 mM mannitol, about 2.2 mM to about 90 mM sodium citrate, about 16 mM to about 30 mM sodium phosphate dibasic; and about 20 mM to about 70 mM glucose where the pH of the aqueous storage solution is above about 8.0.

BRIEF DESCRIPTION OF THE DRAWINGS

FIGS. 5(A)-(D) illustrates graphically ATP levels expressed as a mean percentage of initial values of red blood cell preparations stored in an aqueous storage solution described and a known storage solution herein versus time (days) of storage for samples where the whole blood was held for (A) 8 hours, (B) 12 hours, (C) 16 hours, and (D) 19 hours.

DESCRIPTION OF THE ILLUSTRATED EMBODIMENTS

Figure 1A:
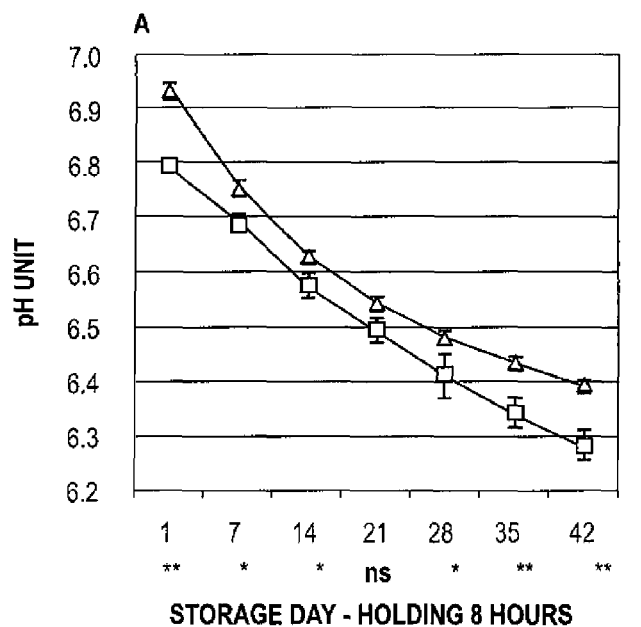
FIGS. 1(A)-(D) illustrate graphically the extracellular pH of red blood cell preparations (compositions) stored in an aqueous storage solution described herein and a known storage solution versus time (days) storage where the whole blood was first held for (A) 8 hours, (B) 12 hours, (C) 16 hours, and (D) 19 hours.

The embodiments disclosed herein are intended to provide only a general description of the aqueous storage solution and methods and apparatus for storing blood components that are the subject of this disclosure. These embodiments are only exemplary, and may be provided in various forms. Therefore, specific details disclosed herein are not to be interpreted as limiting the subject matter of the present disclosure or the appended claims.

The aqueous storage solution and its method of use described herein are useful for the extended storage of red blood cells (e.g. approximately 35 days or greater) that have been separated from whole blood. The solution disclosed herein is particularly useful for the extended storage of red blood cells that have been separated from whole blood that has been held for periods, such as 4 hours, 8 hours or more than 8 hours, including up to 26 hours.

The aqueous storage solution and its method of use are generally applicable to the storage of red blood cells that have been manually separated from whole blood or have been separated using automated collection devices such as the Alyx Separator manufactured and sold by Fenwal Inc. of Lake Zurich Ill. and generally described in U.S. Pat. Nos. 6,348,156; 6,857,191; 7,011,761; 7,087,177 and 7,297,272 and U.S. Patent Application Publication No. 2005/0137516, all of which are incorporated herein by reference.

In one embodiment, an aqueous red blood cell storage medium is provided that includes nutrients, buffers and salts. The synthetic red blood cell storage solution may be an aqueous solution which may include about 3 mM to about 90 mM sodium citrate; about 15 mM to about 40 mM sodium phosphate; about 20 mM to about 140 mM dextrose; about 20 mM to about 110 mM mannitol; and about 1 mM to about 2.5 mM adenine; the storage solution may have a pH of from about 8.0 to about 9.0. The osmolarity of the solution may be from about 200 mOsm/l to about 320 mOsm/l. The storage solution may optionally contain from about 10 mM to about 100 mM acetate. Optionally, guanosine may also be present in the storage solution from about 0.1 mM to about 2 mM. In addition, gluconate may be present from about mM to about 40 mM. Optionally, a combination of acetate and gluconate may be used.

As discussed above, in one embodiment, sodium citrate may be present from about 3 mM to about 90 mM. More particularly, the sodium citrate may be present from about 15 mM to about 70 mM, or from about 18 mM to about 35 mM.

Sodium phosphate may be present from about 15 mM to about 40 mM. More particularly, the sodium phosphate may be present from about 13 mM to about 30 mM, and more typically from about 20 mM to about 28 mM. Examples of sodium phosphate include (but are not limited to) trisodium phosphate, sodium phosphate dibasic and sodium phosphate monobasic. For example, 100 mls of a storage solution having 25 mM sodium phosphate with a pH of approximately 8.4 may contain 355 mg of sodium phosphate dibasic anhydrous ($Na_2HPO_4$). It will be understood that the pH of the storage solution disclosed herein may be adjusted by the amount of the various forms of sodium phosphate (for example, monobasic sodium phosphate, dibasic sodium phosphate, and/or trisodium phosphate) included in the solution.

The pH of the storage solution may be from about 8.0 to about 9.0. More particularly, the pH may be from about 8.1 to about 8.8, or from about 8.3 to about 8.5.

The storage solution may also include an amount of dextrose (glucose). In one embodiment, the dextrose may be present from about 20 mM to about 90 mM. More particularly, the dextrose may be present from about 25 mM to about 75 mM, and more typically from about 35 mM to about 60 mM.

The storage solution described herein may also include from about 20 mM to about 110 mM mannitol. In one embodiment, the mannitol may be present from about 25 mM to about 90 mM, and more typically from about 30 mM to about 60 mM.

In one embodiment, the storage solution may also include from about 1 mM to about 2.5 mM adenine. More particularly, the adenine may be present from about 1.2 mM to about 2.3 mM, and more typically from about 1.3 mM to about 2.1 mM.

Figure 10:
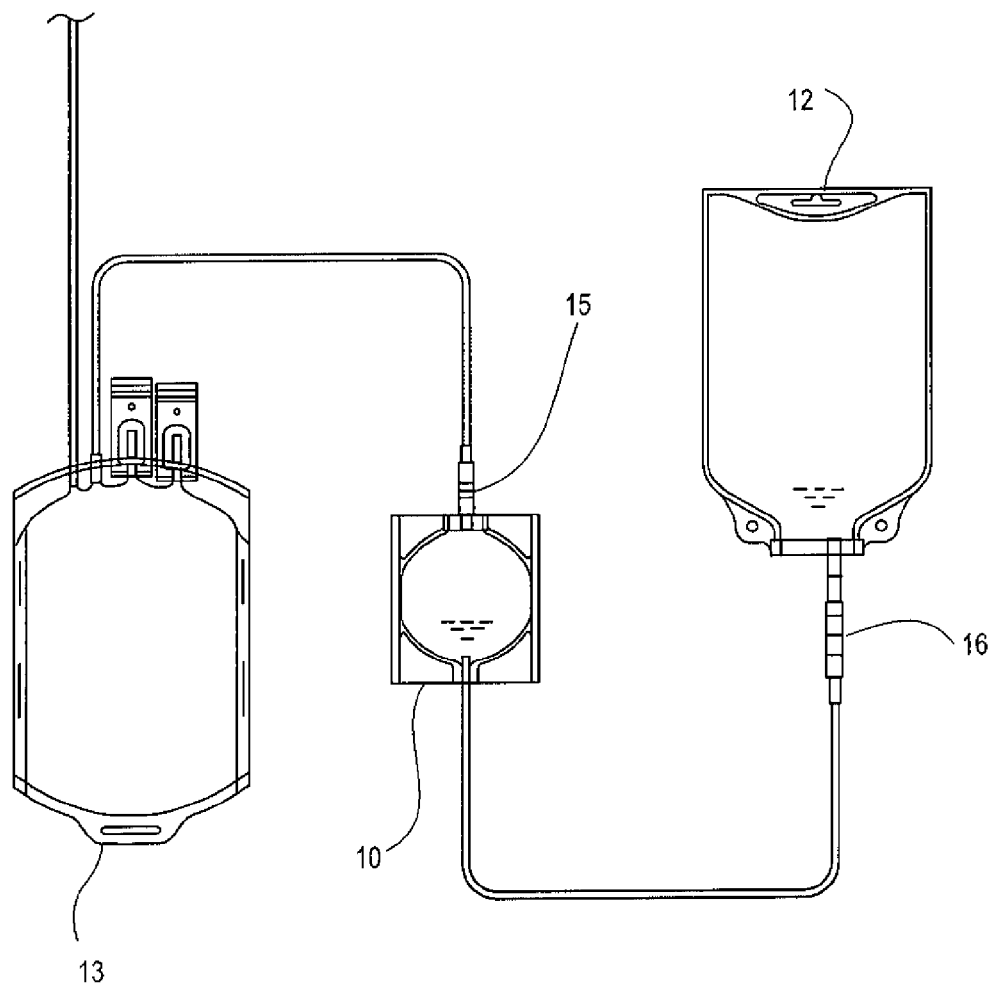
FIG. 10 is a plan view of a disposable tubing and container set useful in the processing of red blood cells.
Figure 11A:
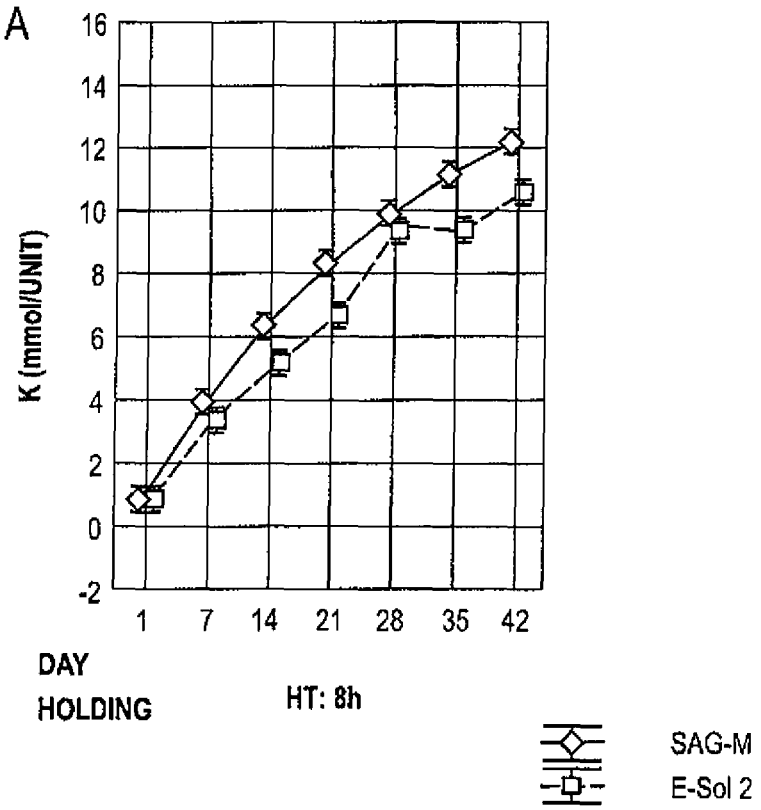
FIG. 11(A)-(D) illustrates graphically levels of extracellular potassium expressed per unit of blood for red blood cell preparations stored in an aqueous solution described herein.
Figure 11B:
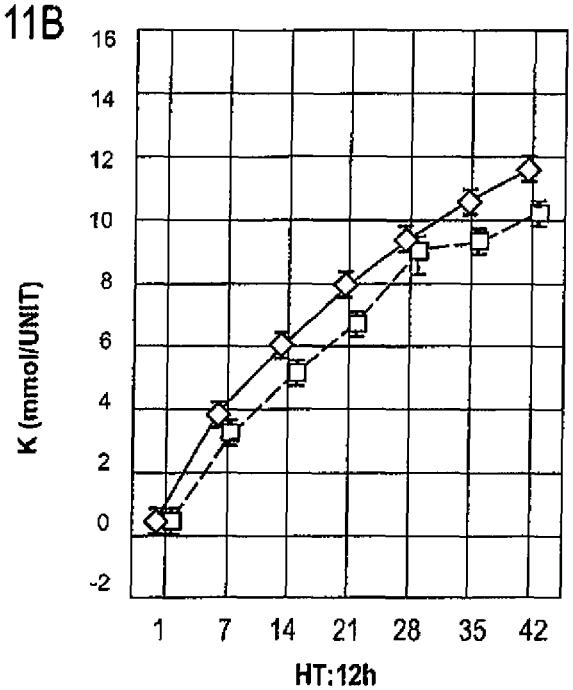
Figure 11C:
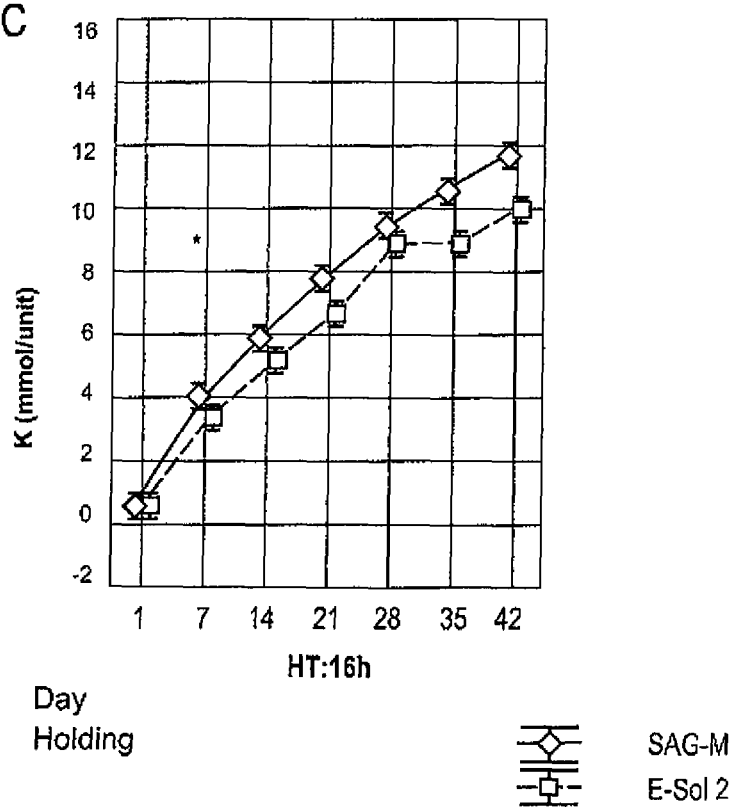
Figure 11D:
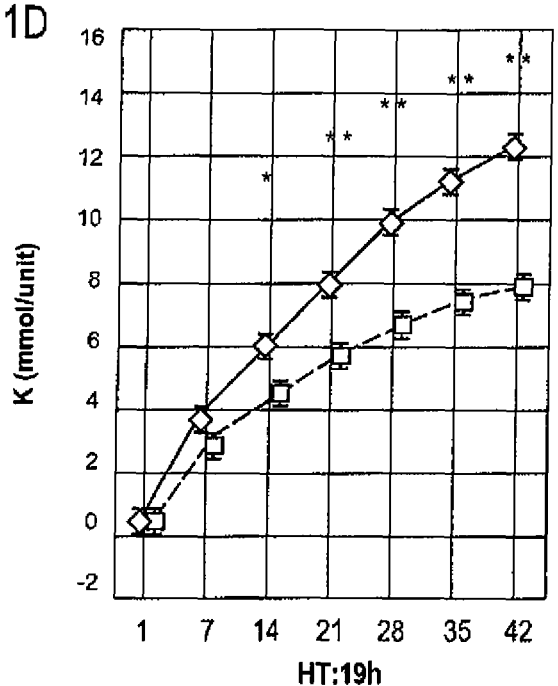

One difficulty that is encountered with storage solutions is in the sterilization of the solutions. Dextrose is known to degrade (caramelize) under autoclaving (heat) sterilization conditions unless it is maintained in an acidic medium. To allow heat sterilization, such as autoclaving, of the dextrose solution, the dextrose solution is preferably acidic e.g., a 7.5% solution with a pH between about 4 to about 6. In some embodiments, dextrose, may be stored in a concentrated solution separately from some or all of the buffered physiological salts of the storage solution. As shown in (FIG. 10), dextrose may be provided in container 10 while the remaining components may be stored as a solution in container 12. By breaking cannula 15, dextrose solution from container 10 may be introduced into container 13. By breaking cannula 16, the remaining components in container 12 are likewise introduced into container 13 by passing the components through now empty container 10. The now reconstituted aqueous storage solution in container 13 may then be combined with the packed red blood cells to provide a red blood cell composition. Alternatively, one may separately introduce the contents of containers 10 and 12 into the red blood cells without prior reconstitution.

An anticoagulant including citrate is typically added to the whole blood prior to processing of the whole blood and its separation into blood components. For example, Citrate-Phosphate-Dextrose or CPD is a commonly used anticoagulant. A unit of whole blood, (450±50 ml per unit) can be collected by methods known to those of skill in the art and about 60 mls to about 70 mls of CPD then being added to each unit of whole blood. As the aqueous red blood cell storage solution disclosed herein includes dextrose and phosphate in some embodiments, the citrate anticoagulant added to whole blood before processing may consist of citrate without phosphate and dextrose, or citrate with phosphate but without dextrose.

In some embodiments, cooling plates may be used after blood collection to reduce the temperature of the whole blood from body temperature, about 37° C., to room temperature, about 20° C. to about 24° C.

To efficiently prepare blood components, the required units of blood are typically accumulated and then processed. Consequently units of whole blood are often held for periods of time until the desired number of units have been accumulated and sufficient resources are available to begin processing. In addition, often more than one blood component is prepared from whole blood, e.g., both red blood cells and platelets. Platelets may only be prepared from blood held at room temperature and, in practice, units of whole blood are often held at room temperature until both red blood cells and platelets will be prepared, although this may not be optimal for the red blood cells. Whole blood may be held for greater than 4 hours, typically 8 or more hours and even 20-26 hours at room temperature (from about 20° C. to about 24° C.) before processing.

In the preparation of red blood cells, leukocyte reduction filters may be used for leukocyte-reduction of whole blood units and/or various fractions prepared from units of whole blood. Red blood cells may be concentrated by standard methods known to one of skill in the art. For example, centrifugation may be used to prepare both a concentrated red blood cell fraction and plasma.

The disclosed red blood cell storage solution may be added to concentrated red blood cells prepared from whole blood. In one embodiment from about 50 mls to about 200 mls of storage solution may be added to concentrated red blood cells prepared from one unit of whole blood. More particularly, from about 75 mls to about 180 mls may be added, or from about 90 mls to about 120 mls may be added. Preferably, and as discussed in greater detail below, approximately 100 to 110 mls of the red cell storage solution disclosed herein are added to red blood cells derived from one unit of whole blood, generally 280 to 350 mls of packed red blood cells.

Table 1 sets forth three exemplary formulations storage solution suitable for addition to the concentrated (packed) red blood cells prepared from one unit of blood. As set forth in Table 1, the solution "E-Sol 3" is provided in a volume of 100 mls, "E-Sol 4" is provided in a volume of 110 ml, and E-Sol 2 is provided in a volume of 150 ml. Table 2 sets forth the amounts of components (in milligrams) with the preferred volumes described above for E-Sol 2, E-Sol 3, and E-Sol 4. Table 2 also provides the amounts and volumes of known red cell storage solution known as SAG-M.

TABLE 1

| Component (mmol/L) | E-Sol 3 | E-Sol 4 | E-Sol 2 |
| --- | --- | --- | --- |
| Sodium Citrate dihydrate, EP | 31.2 | 28.4 | 20.8 |
| Sodium Phosphate dibasic, anhydrous | 25.0 | 22.7 | 16.7 |
| Mannitol, EP | 50.0 | 45.4 | 33.3 |
| Adenine, EP | 2.0 | 1.9 | 1.4 |
| Dextrose, monohydrate, EP | 56.8 | 51.6 | 37.8 |
| | 100 mL | 110 mL | 150 mL |

TABLE 2

|  | SAG-M | E-Sol 2 | E-Sol 3 | E-Sol 4 |
|---|---|---|---|---|
| Sodium citrate dihydrate | — | 918.75 mg | 918.75 | 918.75 mg |
| Glucose monohydrate | 900 mg | 1125 mg | 1125 mg | 1125 mg |
| Sodium acid phos. dihydrate | — | — | — | — |
| Sodium phosphate dibasic, anhydrous | — | 355 mg | 355 mg | 355 mg |
| Adenine | 16.9 mg | 27.5 mg | 27.5 mg | 27.5 mg |
| Mannitol | 525 mg | 910 mg | 910 mg | 910 mg |
| Sodium chloride | 877 mg | — | — | — |
| pH | 4.8 | 8.4 | 8.4 | 8.4 |
| Volume | 100 ml | 150 ml | 100 ml | 110 ml |
| Osmolarity mOsm $L^{-1}$ | 376 | 206 | 309 | 281 |

Red blood cells in storage solutions described herein may be stored for extended periods at temperatures ranging from about 2° C. to about 6° C. In some embodiments, red blood cells may be stored from about 1 to about 60 days. More particularly, the red blood cells may be stored from about 10 to about 58 days, or from about 15 to about 50 days. Typically, the preparations may be stored from about 35 to about 50 days.

By way of example, but not limitation, illustrations of methods of collecting and storing red cells using the storage solution described herein are provided.

EXAMPLE 1

Units of whole blood (450±50 ml per unit) were collected by methods known to those of skill in the art and about 63 mls of CPD was added for each unit of whole blood. The units of whole blood were cooled to room temperature after collection using cooling plates (ThermaSure™, Sebra, Tucson, Ariz., USA), and the whole blood units were then held at room temperature (about 20° C. to about 24° C.) for 8, 12, 16, or 19 hours.

Before concentration of red blood cells, whole blood units were leukocyte-reduced using inline whole blood leukocyte reduction filters. Red blood cells were concentrated using centrifugation to prepare concentrated red blood cell fractions and plasma using a hardspin centrifugation program followed by separation with T-ACE equipment (Terumo, Leuven, Belgium).

In Example 1, two different red blood cell additive solutions were added to the units of red blood cell concentrate: either 150 ml of E-Sol 2 (test) or 100 ml SAG-M (reference) (see Tables 1 and 2). The red blood cell units with additive solutions were then stored from 1 to about 42 or about 49 days at about 2° C. to about 6° C.

In vitro results obtained at the indicated time points over the 42 or 49 days of storage are presented in Tables 3 and 4 and in FIGS. 1-5. Different experimental groups are designated depending on the hold time of whole blood: groups A or E (8 hours hold of whole blood), groups B or F (12 hours hold of whole blood), groups C or G (16 hours hold of whole blood), and groups D or H (19 hours hold of whole blood).

Various in vitro parameters were evaluated using CA 620 Celiguard hematology equipment (Boule Medical, Stockholm, Sweden). White blood cells (WBC) on day 1 were counted in a Nageotte chamber with a standard microscope (Zeiss). The concentrations of glucose, lactate and extracellular potassium were determined using routine blood gas equipment (ABL 705, Radiometer, Copenhagen, Denmark). In addition, the extracellular pH of the stored red blood cells was measured (at 37° C.). A HemoCue plasma/low hemoglobin photometer was used for the analysis of hemolysis (HemoCue Corp., Ängelholm, Sweden). ATP concentrations were determined using a luminometric technique (Orion, Berthold, Pforzheim, Germany) based on methods known in the art. Finally, 2,3-DPG concentrations were analyzed using a spectrophotometer (Roche kit 148334001).

The Kruskal-Wallis Analysis of ranks was used for the comparison of means of measured values between the E-Sol solution and SAG-M stored red blood cell preparations at the different holding times. Data are presented as mean±SEM (n=6 pooled units/group) and the degree of statistical significance for individual samples is designated in Tables 3-4 and FIGS. 1-5 as ns (not significant), * ($p<0,05$),  ($p<0,01$), or * ($p<0,001$).

Certain characteristics (e.g., RBC volume and hemoglobin content) of the stored red blood samples are shown in Table 3 and hemolysis results from samples taken during at the indicated days during storage (up to 42 or 49 days) are presented in Table 4. As shown in Table 4, hematocrits ranged from 47±3% to 48±3% for red blood cell preparations stored in the E-Sol solution of the type disclosed herein compared with 55±2% to 62±2% in for red blood cell preparations stored in the SAG-M groups (Table 4). Table 4 also indicates that hemolysis was lower for red blood cells stored in the E-Sol solution than in SAG-M.

Data reflecting red blood cell function and metabolism are presented in FIGS. 1-5, generally during 42 days of storage. However, 2, 3-DPG measurements were stopped in some groups when 2, 3-DPG levels approached zero and measurements were no longer meaningful, generally after 14-28 days. For each holding time of whole blood, the red blood cells stored in the E-Sol solution (e.g., E-Sol 2) were compared with those of the reference groups, red blood cells stored in SAG-M (SAG-M).

Figure 1B:
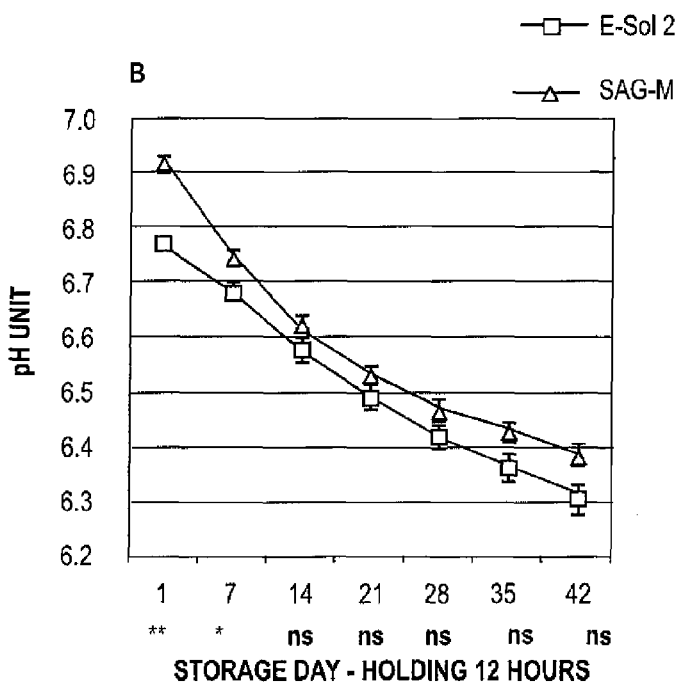
Figure 1C:
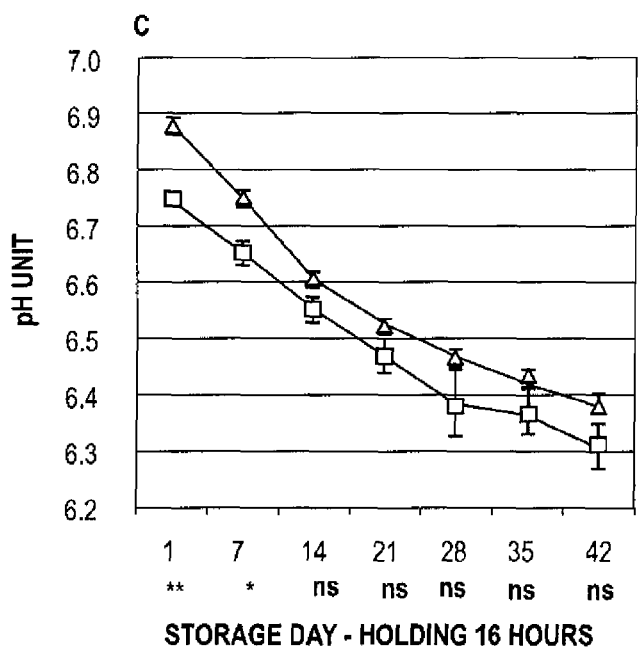
Figure 1D:
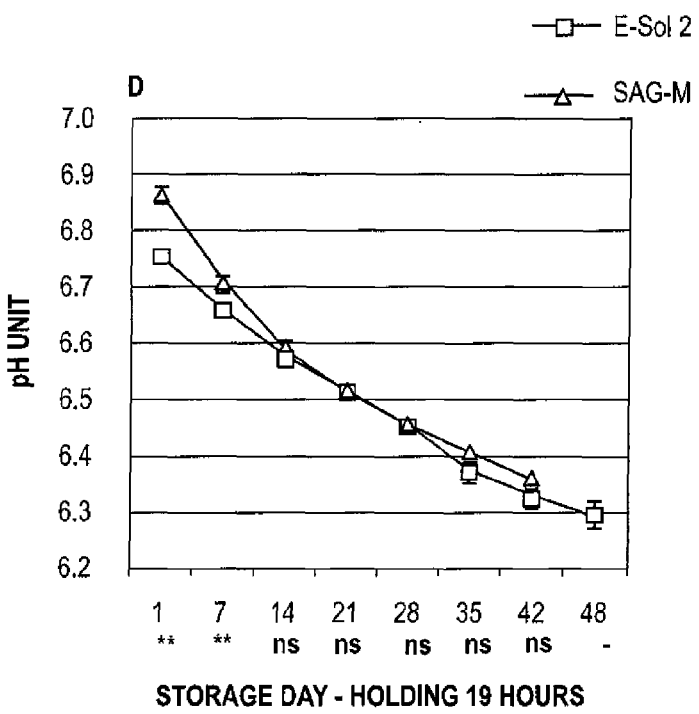

Extracellular pH is one parameter that may be used to assess the functionality of stored red blood cells. As illustrated in FIG. 1(A), red blood cell preparations which had been prepared from whole blood that was held for 8 hours before processing and subsequently stored in the E-Sol solution (e.g., E-Sol 2) displayed lower extracellular pH throughout storage, as compared to the red blood cells in the reference group (SAG-M) which were also prepared from whole blood held for 8 hours but stored in SAG-M. FIGS. 1(B)-(D) illustrate that red blood cells which had been prepared from whole blood that was held for 12 hours (FIG. 1(B)), 16 hours (FIG. 1(C)) or 19 hours (FIG. 1(D)) before processing and subsequently stored in the E-Sol solution displayed statistically significant reduced extracellular pH at days 1 and 7 of storage, as compared to the red blood cells in the reference group (SAG-M) which were also prepared from whole blood held for 12, 16, and 19 hours but subsequently stored in SAG-M. After day 7 of storage there was generally no statistically significant difference in extracellular pH between red blood cells stored in the E-Sol solution and SAG-M except for the whole blood sample held for eight hours. (FIG. 1(A)).

As shown in FIGS. 2(A)-(D), there was generally no statistically significant difference in glucose consumption between samples stored in the E-Sol solution or SAG-M.

Figure 2A:
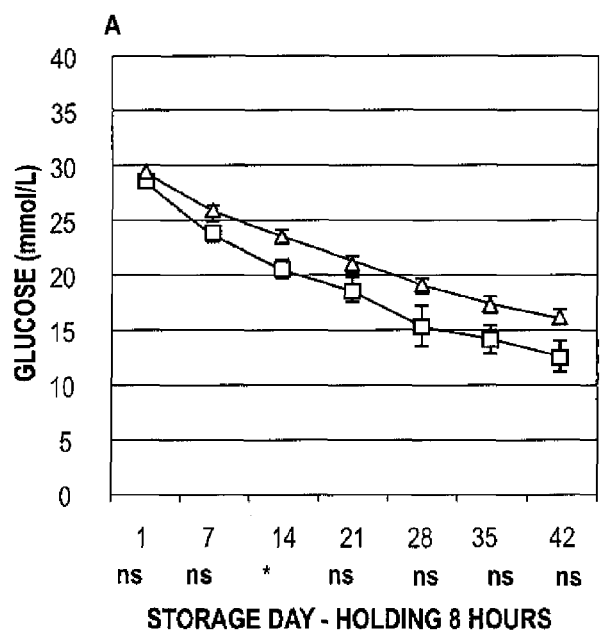
FIGS. 2(A)-(D) illustrate graphically the glucose levels (mmol/L) of red blood cell preparations stored in an aqueous storage solution described herein and a known storage solution versus time (days) of storage where the whole blood was held for (A) 8 hours, (B) 12 hours, (C) 16 hours, and (D) 19 hours.
Figure 2B:
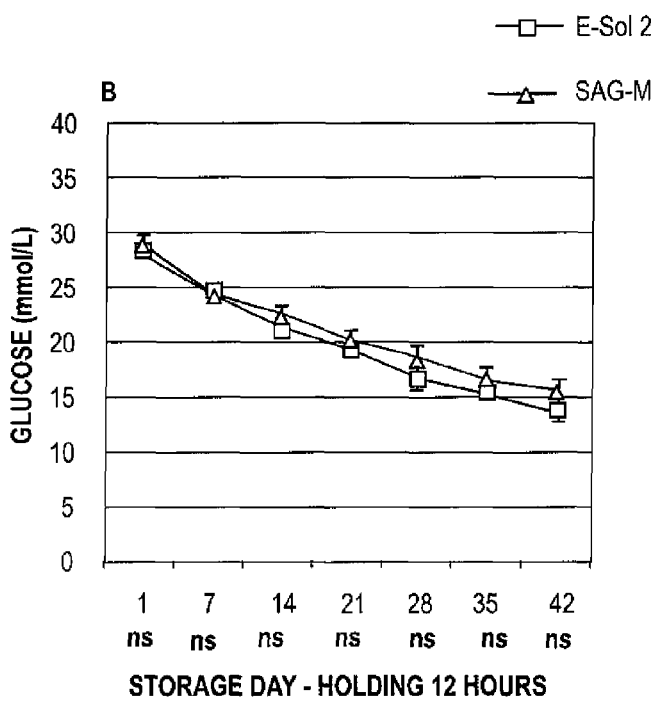
Figure 2C:
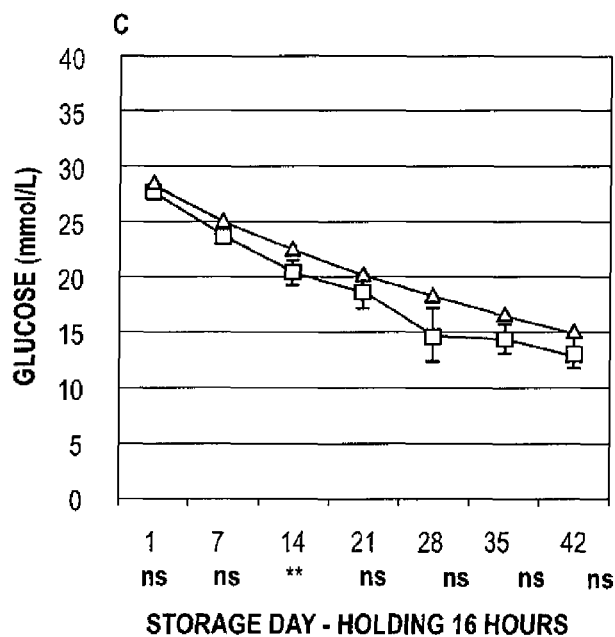
Figure 2D:
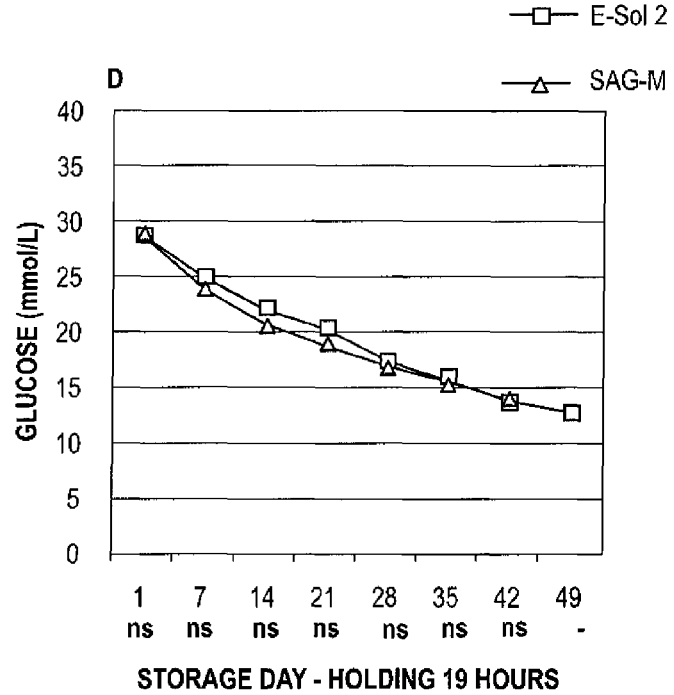
Figure 2E:
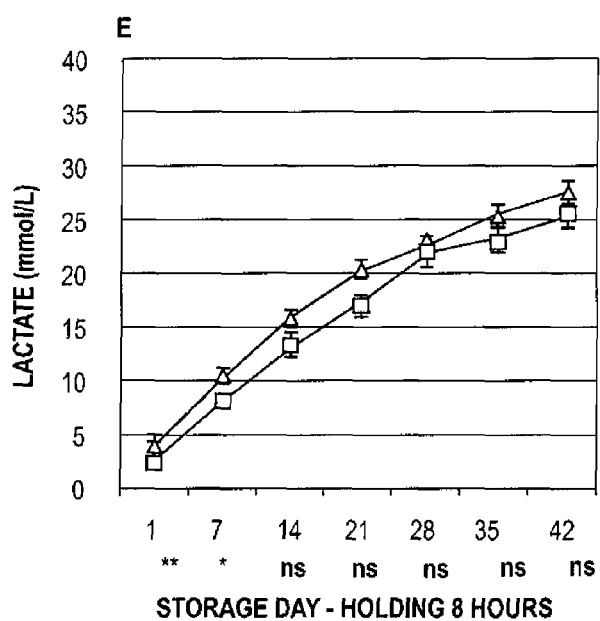
FIGS. 2(E)-(H) illustrate graphically the lactate levels (mmol/L) of red blood cell preparations stored in an aqueous storage solution described herein and a known storage solution versus (days) of storage for samples where the whole blood was held for (E) 8 hours, (F) 12 hours, (G) 16 hours, and (H) 19 hours.
Figure 2F:
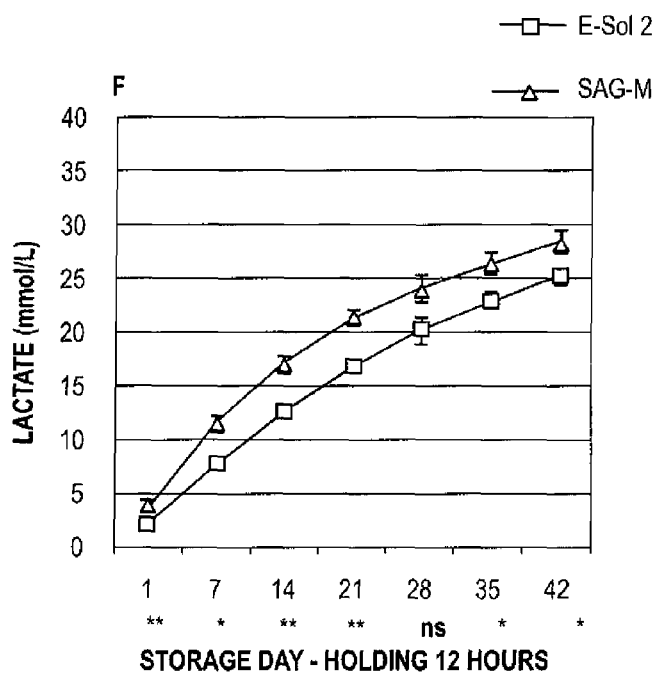
Figure 2G:
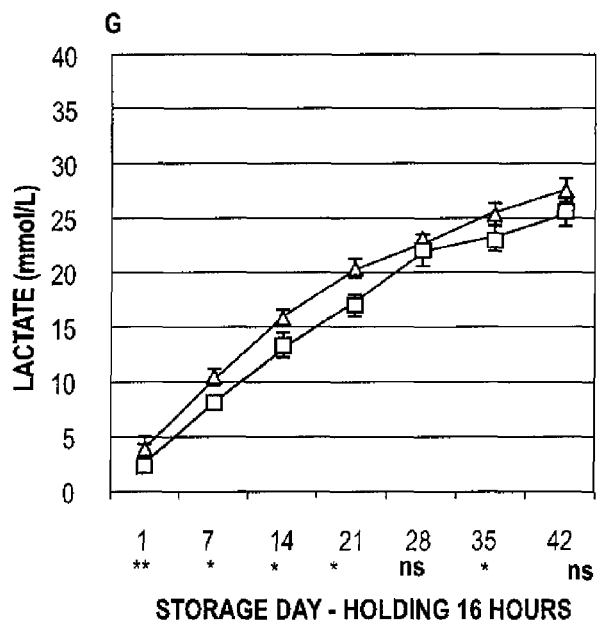
Figure 2H:
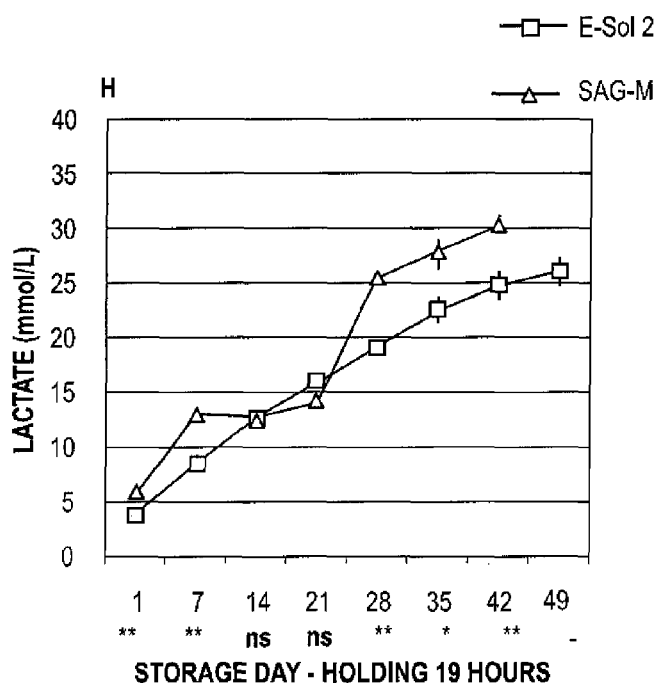

Lactate levels are measured as a further indication of the properties of stored cells, with higher lactate levels possibly indicating that the cells are using the less efficient anaerobic glycolysis pathway. As illustrated in FIG. 2(E), red blood cells which had been prepared from whole blood that was held for 8 hours before processing and subsequently stored in a solution as disclosed herein (e.g., E-Sol 2) displayed reduced levels of lactate at days 1 and 7 of storage, as compared to the red blood cells in the reference group (SAG-M) which were also prepared from whole blood held for 8 hours but subsequently stored in SAG-M. FIGS. 2(F)-(H) illustrate that red blood cells which had been prepared from whole blood held for 12 hours (FIG. 2(F)), 16 hours (FIG. 2(G)) or 19 hours (FIG. 2(H)) before processing and subsequently stored in E-Sol 2 displayed statistically significant reduced levels of lactate throughout the majority of the storage period, as compared to the red blood cell preparations in the reference group (SAG-M) which were also prepared from whole blood held for 12, 16, and 19 hours but subsequently stored in SAG-M.

Adenosine triphosphate (ATP) levels were also measured, with higher ATP levels generally predicting better cell functionality. As illustrated in FIGS. 3 (A)-(C), storage of red blood cells in an E-Sol solution of the type described herein generally results in increased levels of ATP as compared to red blood cells stored in SAG-M. For red blood cells prepared from whole blood held for 8 hours (FIG. 3(A)) before processing, subsequent storage in the E-Sol solution as compared to storage in SAG-M results in statistically significant increased ATP concentrations from day 14 through day 42. For red blood cells prepared from whole blood held for 12 hours (FIG. 3(B)) before processing, storage in an E-Sol solution as compared to storage in SAG-M results in statistically significant increased ATP concentrations at days 21, 35, and 42 of storage. For red blood cells prepared from whole blood held for 16 hours (FIG. 3(C)) before processing, storage in an E-Sol solution as compared to storage in SAG-M resulted in statistically significant increased initial ATP concentrations which persisted through day 14.

In red blood cell preparations stored in an E-Sol solution as described herein, concentrations of 6-7 µmol ATP/g hemoglobin were seen during 5 weeks of storage (FIG. 3(A)-(D)), well above the level where adverse consequences may occur (below 2-3 µmol ATP/g hemoglobin; Hess et al.; Transfusion 2002; 42: 747-752.)

Figure 4A:
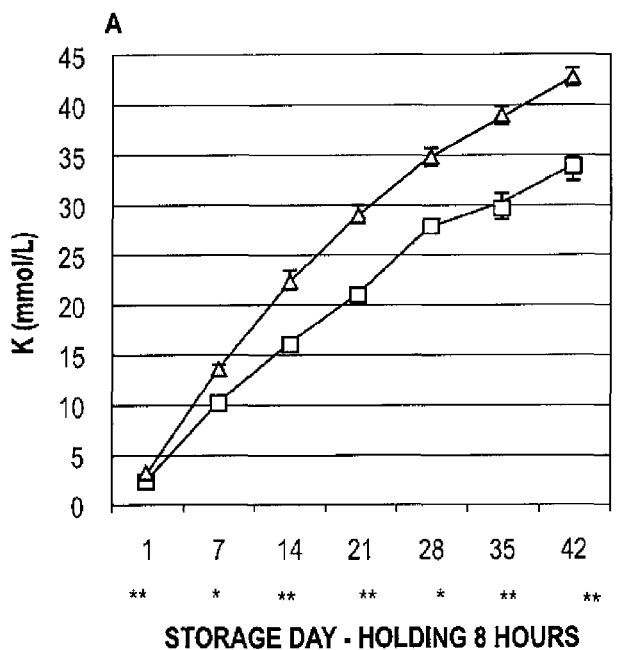
FIGS. 4(A)-(D) illustrates graphically the extracellular potassium concentration (mmol/L) of red blood cell preparations stored in an aqueous storage solution described herein and a known storage solution versus time (days) of storage for samples where the whole blood was held for (A) 8 hours, (B) 12 hours, (C) 16 hours, and (D) 19 hours.
Figure 4B:
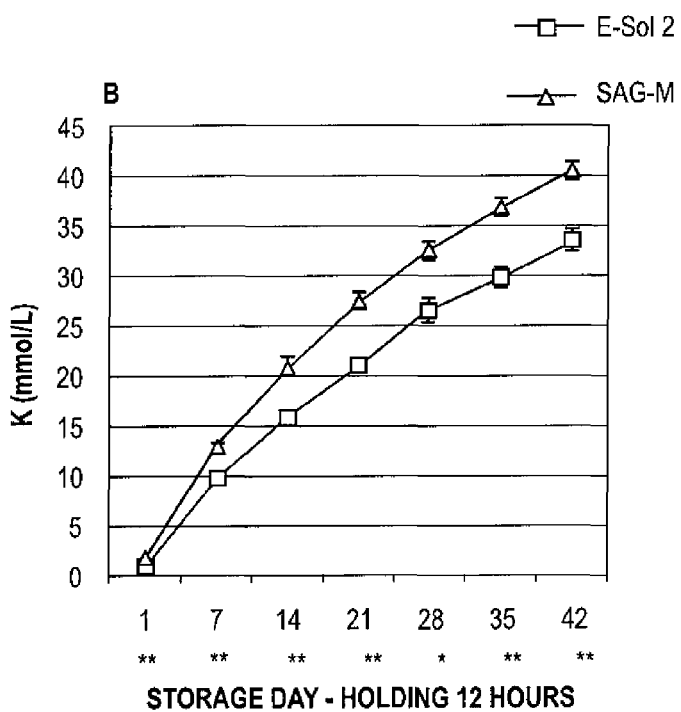
Figure 4C:
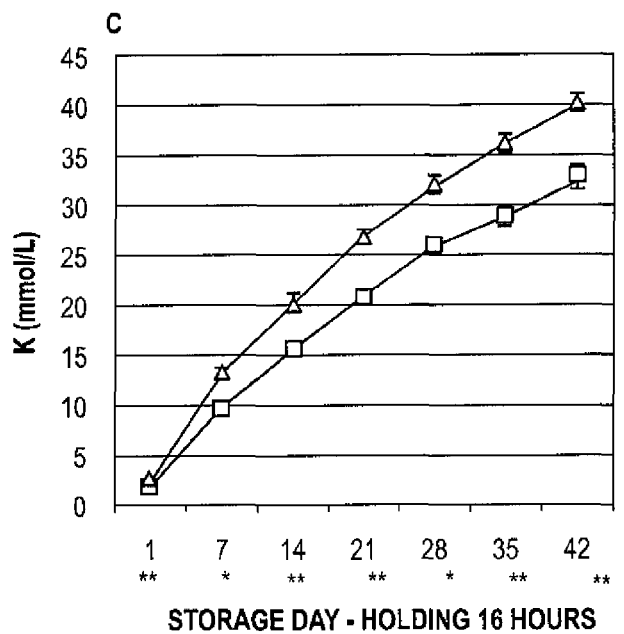
Figure 4D:
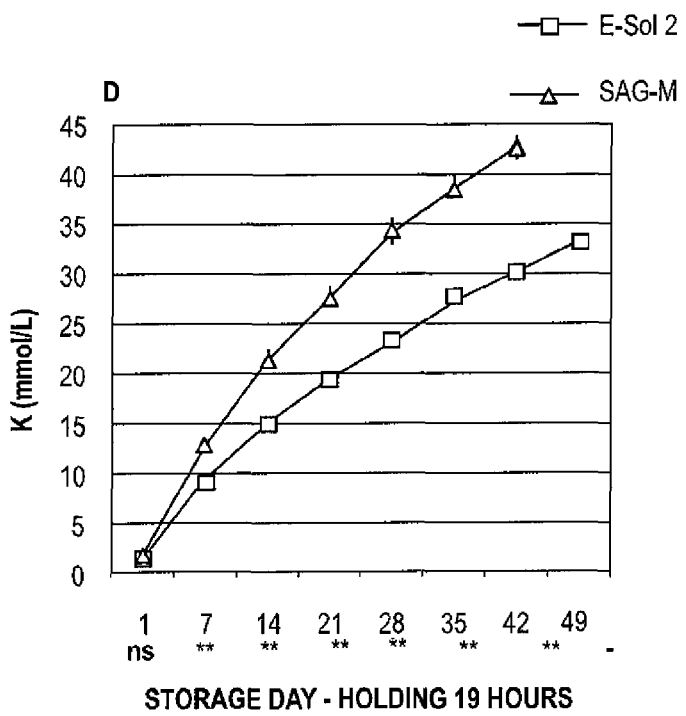
Figure 5A:
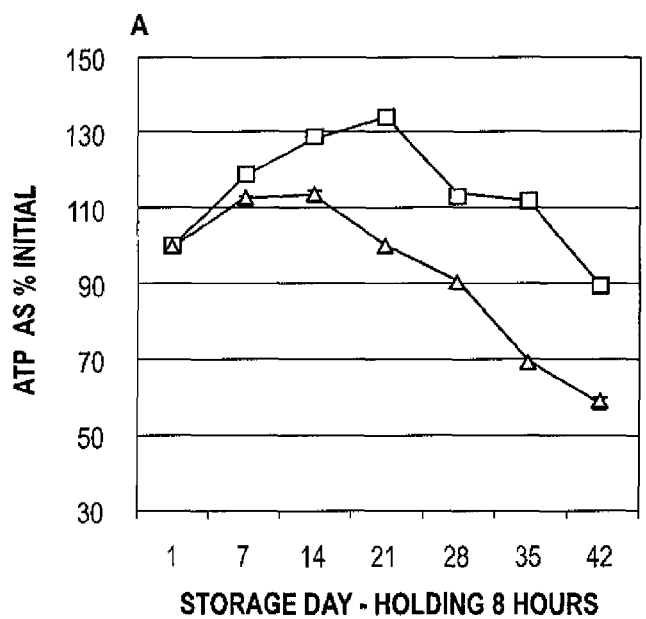
Figure 5B:
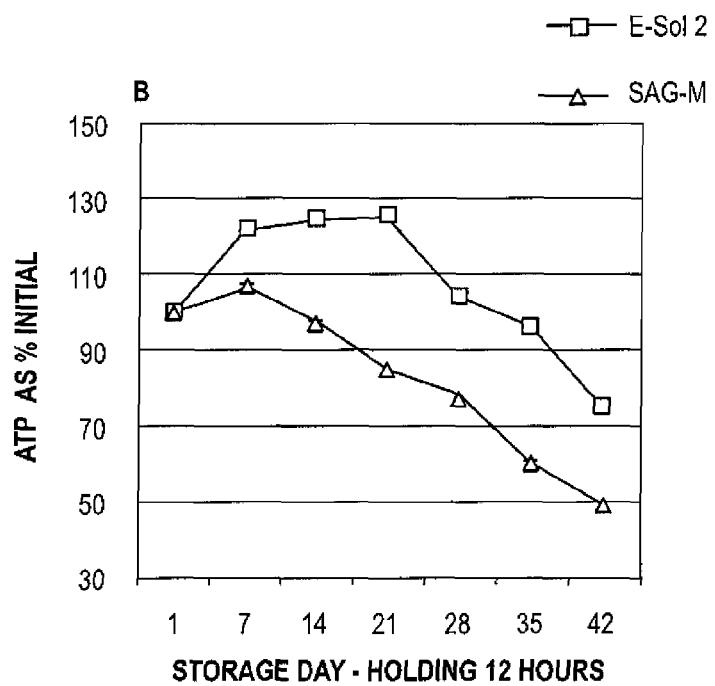
Figure 6:
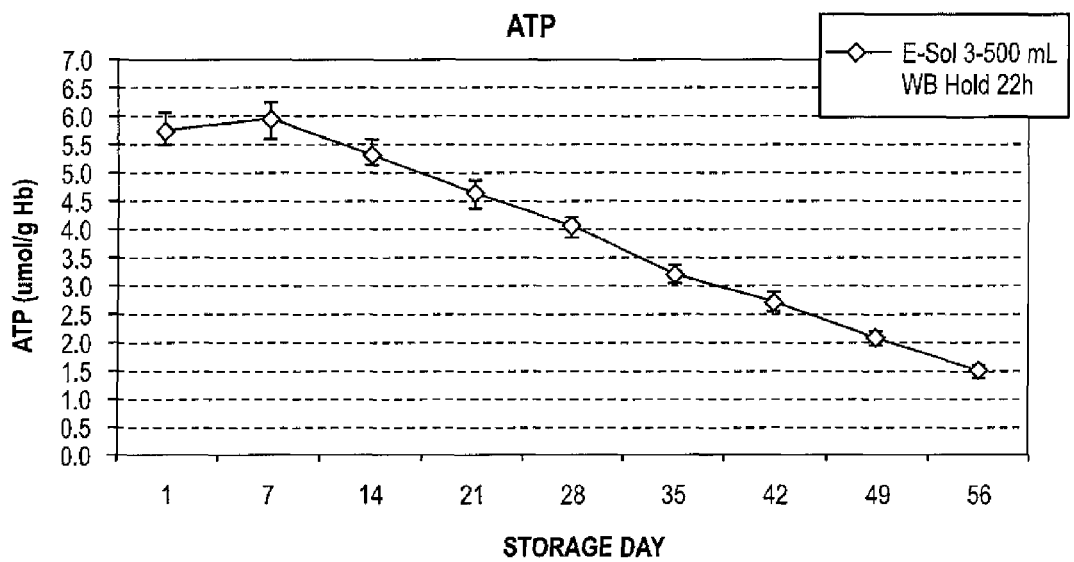
FIG. 6 illustrates graphically ATP levels (μmol/g Hb) versus time (days) for red blood cell preparations stored in an aqueous solution described herein.

As illustrated in FIGS. 4(A)-(D), blood cells which had been prepared from whole blood that was held for 8 (FIG. 4(A)), 12 (FIG. 4(B)), 16 (FIG. 4(C)), or 19 hours (FIG. 4(D)) before processing and subsequently stored in an E-Sol solution displayed statistically significant reduced levels of extracellular potassium throughout storage, as compared to the red blood cells in the reference group (SAG-M) which were also prepared from whole blood held for the same period but subsequently stored in SAG-M. This result is also statistically significant if potassium concentration is determined as function of the number of units of blood (mmol/unit of blood). (FIG. 11). As increased extracellular potassium levels are believed to be predictive of decreased cell viability and increased hemolysis, these results are a further indication that the solutions described herein are preferable to certain storage solutions such as SAG-M.

In FIGS. 5(A)-(D), the ATP levels in red blood cells during storage are shown as the mean percentage of the initial (day 1 of storage) mean ATP concentration of each set of samples. For red blood cells prepared from whole blood held for 8 (FIG. 5(A)), 12 (FIG. 5(B)), 16 (FIG. 5(C)), or 19 (FIG. 5(D)) hours and subsequently stored in a solution as described herein (e.g., E-Sol 2), the mean levels of ATP remained well above 50% of mean initial (day 1) levels, even after 42 days of storage. In contrast, for red blood cell preparations held for 12 (FIG. 5(B)), 16 (FIG. 5(C)), or 19 (FIG. 5(D)) hours and subsequently stored in SAG-M, mean ATP levels fell to less than 50% of mean initial levels by day 42 of storage. Only the red blood cells prepared from whole blood held for 8 hours and subsequently stored in SAG-M maintained mean ATP levels above 50% of the mean initial value by day 42 of storage. These results indicate that storage of red blood cells in solutions of the type described herein are preferable for maintaining ATP levels throughout storage.

Figure 3A:
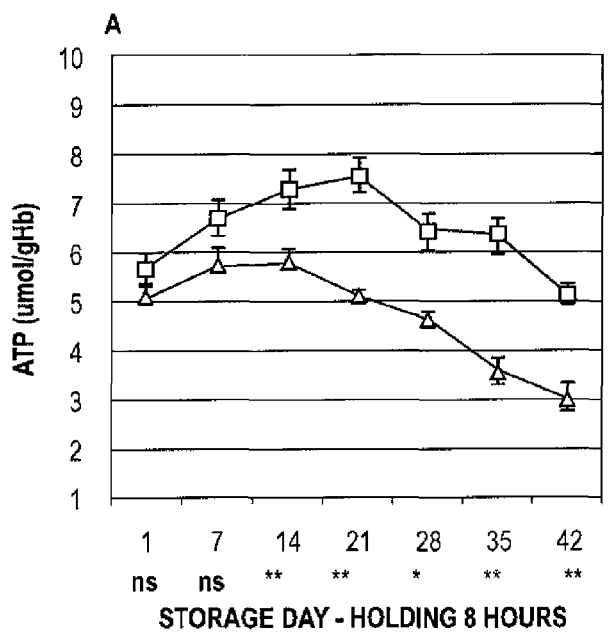
FIGS. 3(A)-(D) illustrates graphically the ATP concentrations (μmol/g Hb) of red blood cell preparations stored in an aqueous storage solution and a known storage solution described herein versus time (days) of storage for samples where the whole blood was held for (A) 8 hours, (B) 12 hours, (C) 16 hours, and (D) 19 hours.
Figure 3B:
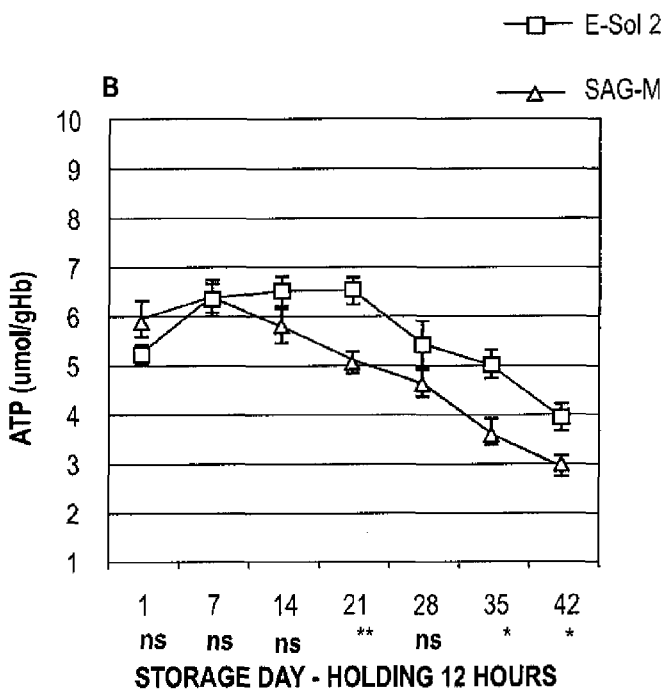
Figure 3C:
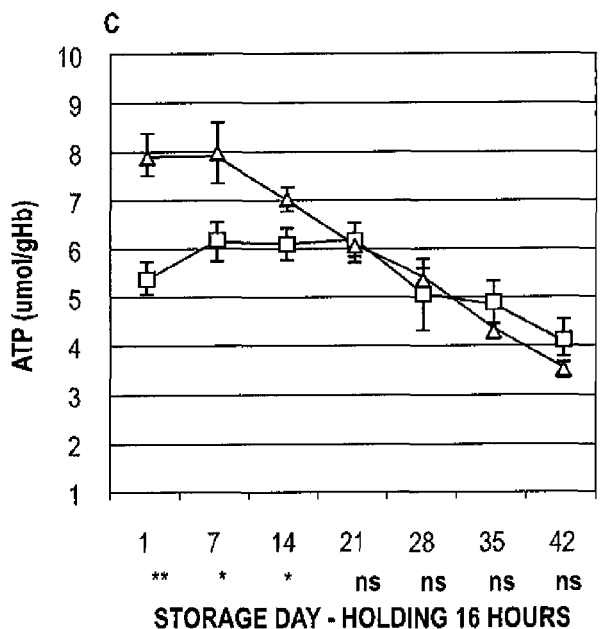
Figure 3D:
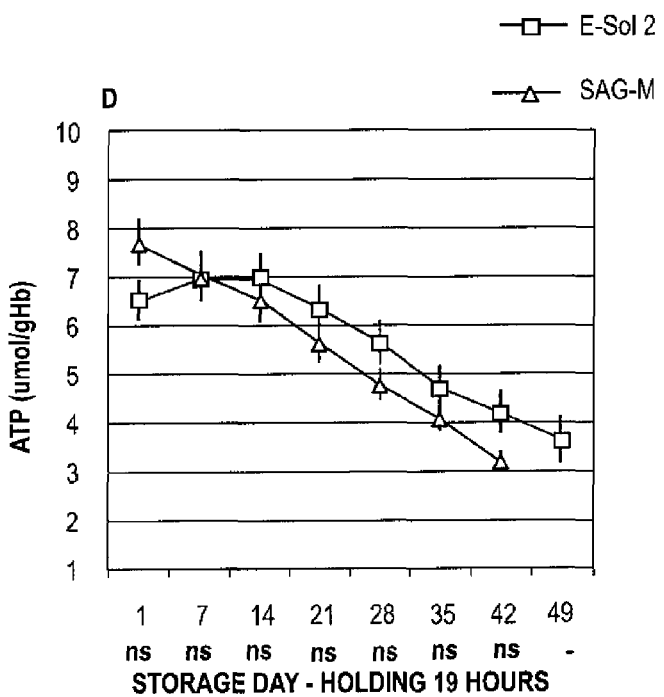
Figure 3E:
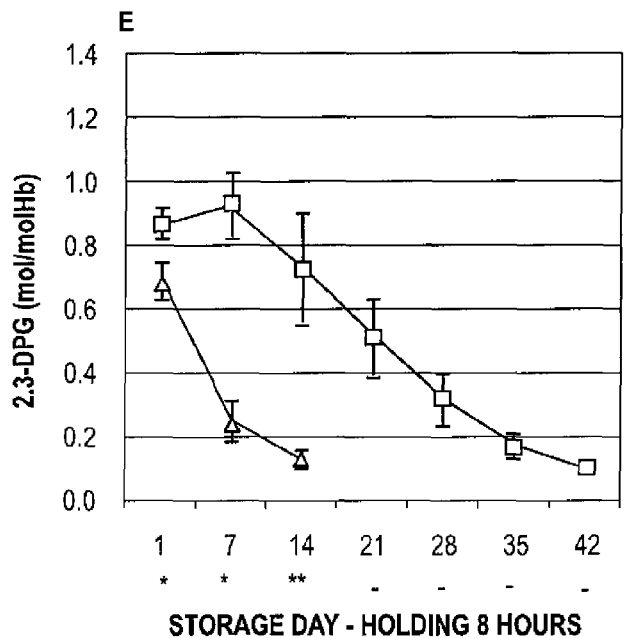
FIGS. 3(E)-(H) illustrates graphically the 2-3DPG concentrations (mol/mol Hb) of red blood cell preparations stored in an aqueous storage solution as described herein and a known storage solution versus time (days) of storage for samples where the whole blood was held for (E) 8 hours, (F) 12 hours, (G) 16 hours, and (H) 19 hours.
Figure 3F:
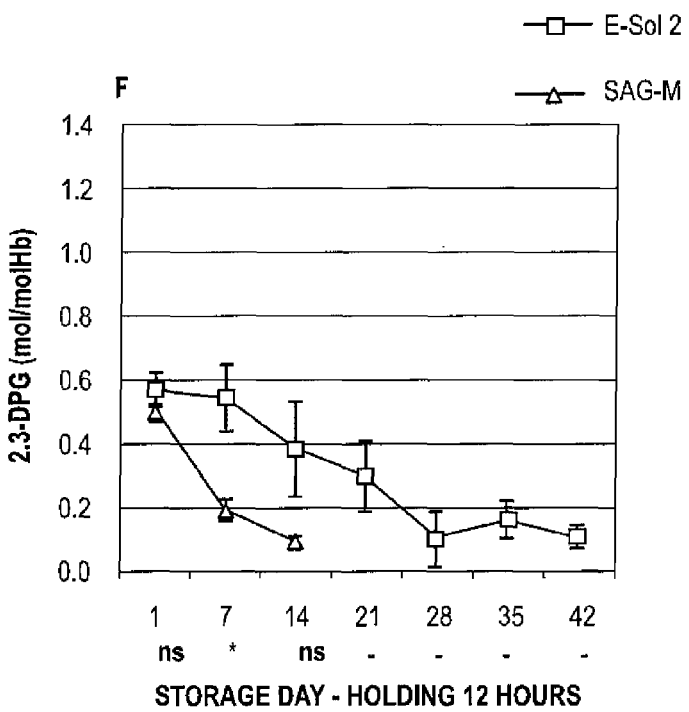
Figure 3G:
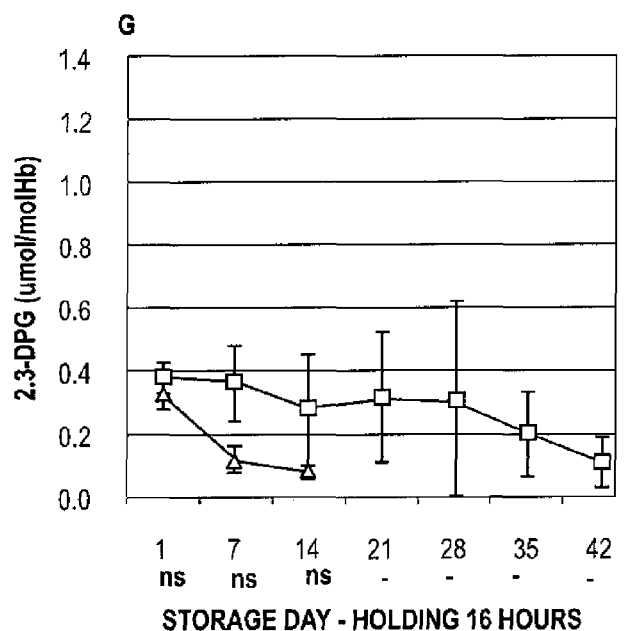
Figure 3H:
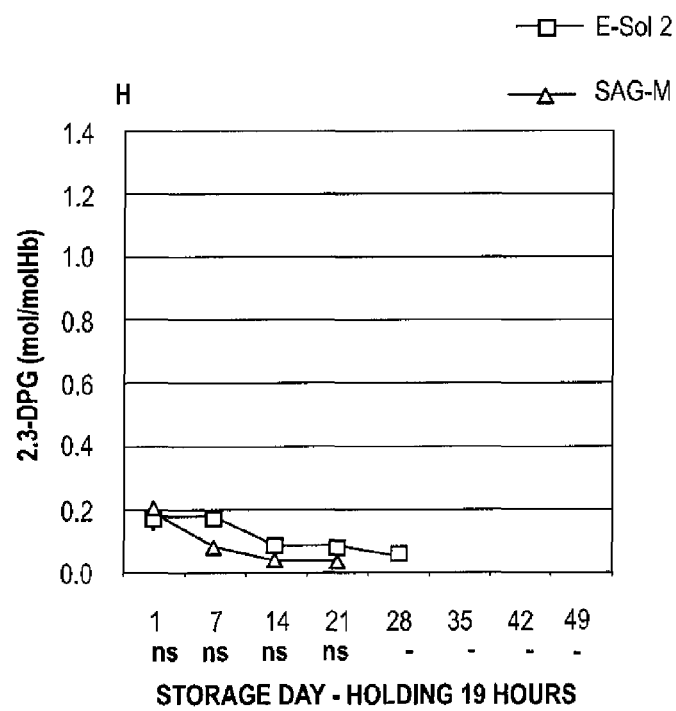

2, 3-diphosphoglycerate (2, 3-DPG) is a further parameter used to measure the properties of stored cells. Red blood cells depleted of 2, 3-DPG will have a left-shifted oxygen dissociation curve that is associated with increased oxygen affinity and probably a less effective supply of oxygen to cells and tissues. After transfusion, red blood cells with low 2, 3-DPG levels are thought to normalize within 2-3 days. (Högman et al.; Transfus Med Rev 1999: 13:275-296.) As illustrated in FIG. 3(E), storage of red blood cells prepared from whole blood held for 8 hours and subsequently stored in an E-Sol solution of the type as disclosed herein (e.g., E-Sol 2) resulted in statistically significant higher concentrations of 2, 3-DPG, as compared to the red blood cells prepared from whole blood held for 8 hours but subsequently stored in SAG-M. 2, 3-DPG is present for about 10 days in SAG-M when red blood cells are prepared within 8 hours after blood collection whereas 2,3-DPG levels appear to be maintained for at least 21 days for red blood cells stored in the E-Sol solution. In addition, FIGS. 3(F)-(G) indicate that red blood cells prepared from whole blood held for 12 and 16 hours respectively also displayed statistically significant higher concentrations of 2, 3-DPG when stored in an E-Sol solution than when stored in SAG-M. For instance, statistically significant higher levels of 2, 3 DPG were observed in red blood cells prepared from whole blood held for 12 hours and stored in an E-Sol solution, than that observed in red blood cells prepared from whole blood held for either 8 or 12 hours and subsequently stored in SAG-M (FIGS. 3 (E) and (F)).

Results from this study appear to indicate that as compared to SAG-M, the solutions described herein are more effective red blood cell storage solutions after the whole blood has been first held for a period of time. For example, as shown and discussed above, red blood cells prepared from whole blood held for 8 hours and then stored in an E-Sol solution (e.g., E-Sol 2) displayed improvement in ATP and 2,3-DPG levels as compared to storage in SAG-M under the same conditions (see for example, FIG. 3). Red blood cells prepared from whole blood held for 8 hours at room temperature and stored in an E-Sol solution have in vitro characteristics which are similar to or better than those for blood that has not been held. These in vitro characteristics, such as the concentrations of ATP and 2, 3-DPG, appear to be maintained for several weeks. Similarly, red blood cells prepared from whole blood held for 12 hours before processing and subsequently stored in an E-Sol solution have higher concentrations of ATP and 2, 3-DPG than red blood cells prepared from whole blood held for either 8 or 12 hours and then stored in SAG-M over the entire storage period. In addition, reduced levels of hemolysis were observed at day 42 of storage for red blood cells stored in E-Sol 2 as compared to red blood cells stored in SAG-M. For instance, red blood cells prepared after holding whole blood for 12 hours at room temperature and then stored in an E-Sol solution of the type disclosed herein (e.g., E-Sol 2) displayed lower levels of hemolysis at day 42 of storage than red blood cells prepared from whole blood held for only 8 hours and subsequently stored in SAG-M.

TABLE 3

RBC Volume and Total Hemoglobin content (g/unit) in RBC units stored in SAG-M and E-Sol 2 at day 1.

| Whole blood holding | 8 h | 12 h | 16 h | 19 h |
|---|---|---|---|---|
| RBC volume (ml) | | | | |
| SAG-M | 284 ± 15 | 286 ± 17 | 290 ± 15 | 288 ± 18 |
| E-Sol 2 | 336 ± 12 | 332 ± 12 | 338 ± 10 | 342 ± 22 |
| P | ** | ** | ** | * |
| RBC haemoglobin content (g/unit) | | | | |
| SAG-M | 51 ± 4 | 52 ± 5 | 53 ± 4 | 57 ± 5 |
| E-Sol 2 | 52 ± 5 | 51 ± 3 | 53 ± 4 | 54 ± 6 |
| P | NS | NS | NS | NS |

Six units were included in each group except for "E-Sol 2, 19 h" (5 units).
P - result of Mann-Whitney U-test comparing E-Sol 2 and SAG-M at each holding time.
NS means not significant -
* for P < 0.05,
** for P < 0.01 and
*** for P < 0.001.

blood. The whole blood was then held at room temperature (approximately 22° C.) for 21-23 hours. Concentrated red blood cells were prepared from each unit by centrifugation using standard methods. For each unit of whole blood, 100 mls of storage solution of the type disclosed herein (e.g., E-Sol 3 of Table 2) was added to the concentrated red blood cells. The resuspended cells were then held for 2 hours at room temperature and then passed through a filter (soft housing red cell filter, Fenwal) to deplete leukocytes. The leukocyte-depleted red blood cell fraction was then stored (RBC storage bag, Optipure RC Set, Fenwal) at 4° C. until the completion of the study.

Samples were taken during processing and at days 1, 7, 14, 21, 28, 35, 42, 49, and 56 for analysis of intracellular ATP levels, hemolysis, glucose and lactate concentration by methods known to those of skill in the art and as described previously. (See, Högman et al., 2002 Transfusion Vol. 42 pg. 824-829, for an example of sample processing). The characteristics of the red blood cell preparations are shown in Table 5 and results of assays obtained from samples during storage are seen in Table 6 and FIGS. 6-9.

On day 1, all tested red blood cell samples passed the European Union requirements for hematocrit, minimum level of hemoglobin, residual contaminating leukocytes, and reduced hemolysis (Table 6 and FIGS. 6-9)

TABLE 4

Hemolysis in RBC units during storage in SAG-M and E-Sol 2.

| | | Storage day | | | | | | | |
|---|---|---|---|---|---|---|---|---|---|
| | Whole Blood Holding | 0 | 7 | 14 | 21 | 28 | 35 | 42 | 49 |
| | | Hemolysis (%) | | | | | | | |
| SAG-M | 8 h (A) | 0.08 ± 0.01 | 0.08 ± 0.02 | 0.12 ± 0.05 | 0.14 ± 0.05 | 0.16 ± 0.05 | 0.21 ± 0.06 | 0.30 ± 0.05 | — |
| E-Sol 2 | 8 h (A) | 0.10 ± 0.01 | 0.11 ± 0.01 | 0.12 ± 0.04 | 0.11 ± 0.01 | 10.14 ± 0.05 | 0.13 ± 0.04 | 0.16 ± 0.04 | — |
| P | | * | ns | ns | ns | ns | * | ** | — |
| SAG-M | 12 h (B) | 0.08 ± 0.01 | 0.18 ± 0.08 | 0.26 ± 0.15 | 0.31 ± 0.18 | 0.29 ± 0.13 | 0.49 ± 0.23 | 0.52 ± 0.17 | — |
| E-Sol 2 | 12 h (B) | 0.10 ± 0.01 | 0.11 ± 0.02 | 0.20 ± 0.11 | 0.19 ± 0.08 | 0.17 ± 0.10 | 0.27 ± 0.11 | 0.23 ± 0.08 | — |
| P | | ** | ns | ns | ns | ns | ns | * | — |
| SAG-M | 16 h (C) | 0.08 ± 0.03 | 0.12 ± 0.06 | 0.20 ± 0.14 | 0.29 ± 0.09 | 0.38 ± 0.15 | 0.41 ± 0.10 | 0.53 ± 0.16 | — |
| E-Sol 2 | 16 h (C) | 0.23 ± 0.32 | 0.21 ± 0.20 | 0.30 ± 0.39 | 0.35 ± 0.36 | 0.12 ± 0.04 | 0.42 ± 0.47 | 0.41 ± 0.45 | — |
| P | | * | ns | ns | ns | * | ns | ns | — |
| SAG-M | 19 h (D) | 0.07 ± 0.02 | 0.20 ± 0.07 | 0.18 ± 0.08 | 0.26 ± 0.13 | 0.31 ± 0.14 | 0.41 ± 0.18 | 0.54 ± 0.22 | — |
| E-Sol 2 | 19 h (D) | 0.10 ± 0.01 | 0.16 ± 0.12 | 0.18 ± 0.17 | 0.19 ± 0.20 | 0.22 ± 0.27 | 0.26 ± 0.34 | 0.34 ± 0.40 | 0.44 ± 0.51 |
| P | | * | ns | ns | ns | ns | ns | ns | — |

Six units were included in each group except for "E-Sol 2, 19 h" (5 units).
p - Result of Kruskal-Wallis test comparing E-Sol 2 and SAG-M at each holding time
Ns means not significant -
* for p < 0.05,
** for p < 0.01,
*** for p < 0.001

EXAMPLE 2

Figure 7:
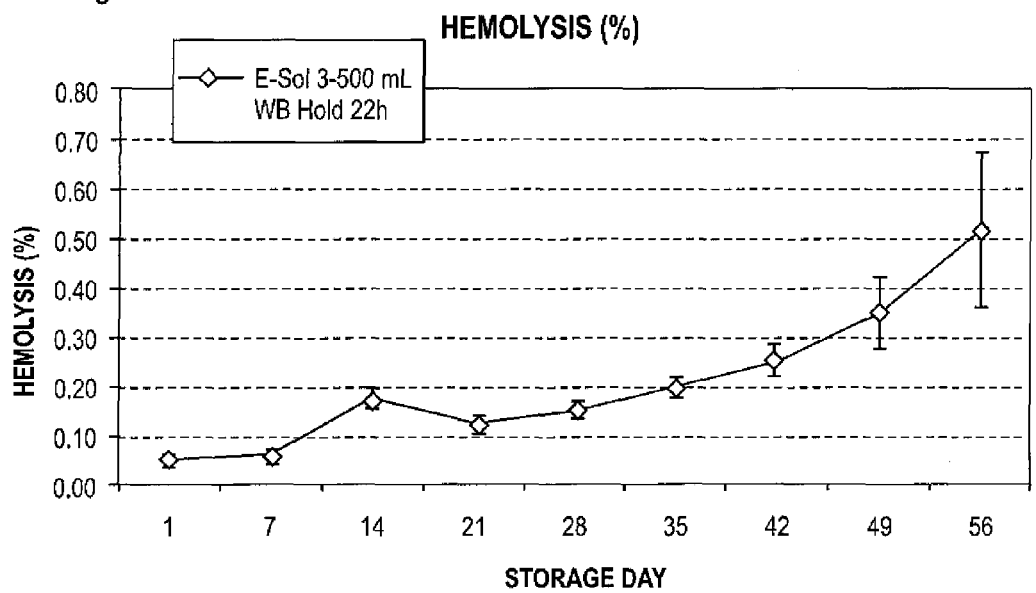
FIG. 7 illustrates graphically percent hemolysis versus time (days) for red blood cell preparations stored in an aqueous solution described herein.
Figure 8:
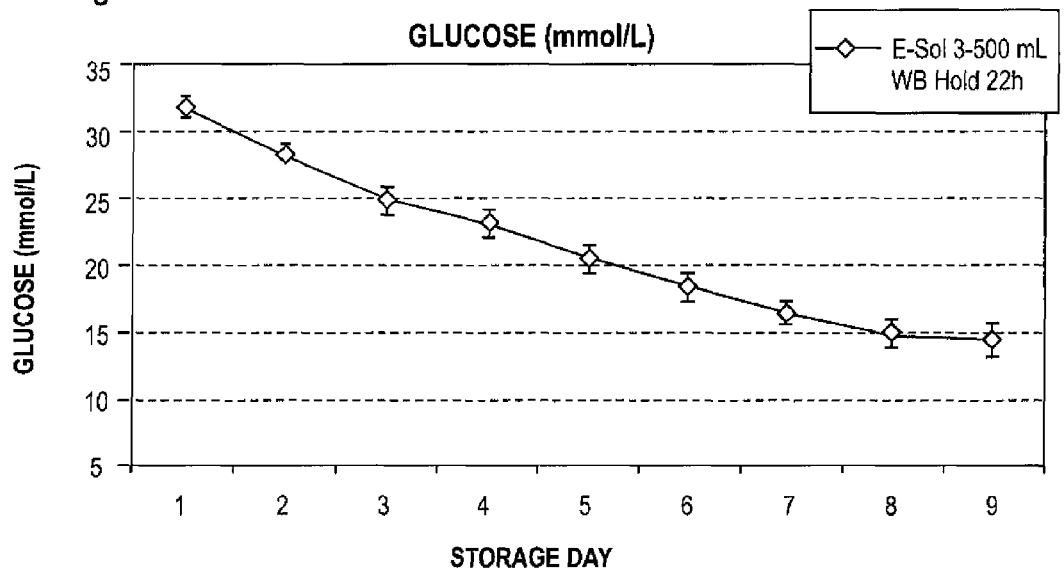
FIG. 8 illustrates graphically glucose levels (mmol/L) versus time (days) for red blood cell preparation stored in an aqueous solution described herein.
Figure 9:
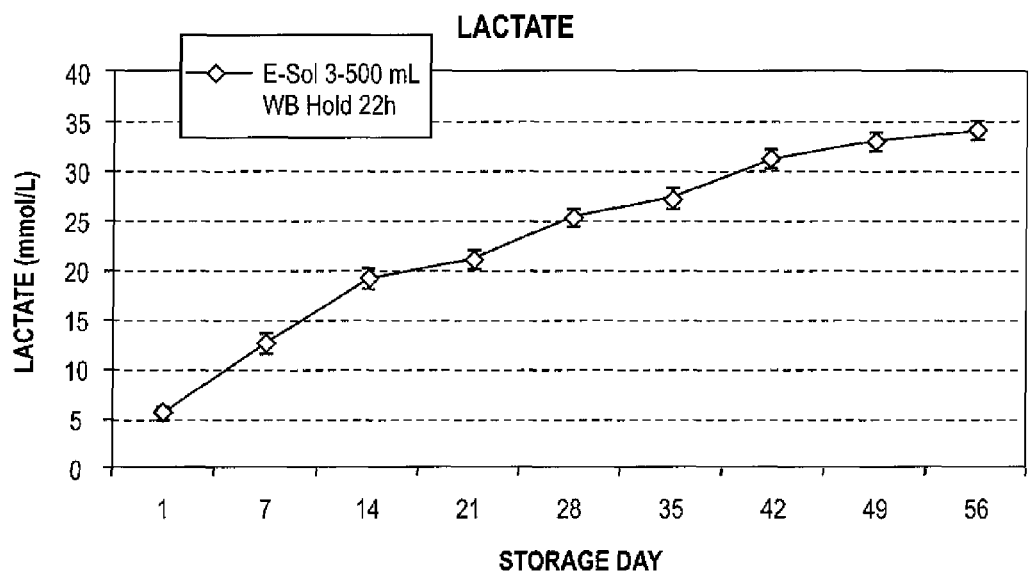
FIG. 9 illustrates graphically lactate levels (mmol/L) versus time (days) for red blood cell preparation stored in an aqueous solution described herein.

In another example, six units of whole blood were collected by methods known to those of skill in the art using approximately 70 mls of CPD anticoagulant per unit of whole During storage in an E-Sol solution (e.g., E-Sol 3) hemolysis of the red blood cells rose to 0.52±0.38% on day 56, which was still below the EU (European Union) required limit (Table 6 and FIG. 7). In ⅙ of these units hemolysis was >0.8%. Glucose was adequate even at day 56 (Table 6 and FIG. 8).

TABLE 5

| Parameter | EP QC criteria | Whole Blood | Before Erythro-Sol3 | After Erythro-Sol3 | Leuko-reduce RCC |
|---|---|---|---|---|---|
| Volume (mL) | — | 500 ± 1.4 | 203 ± 19 | 3264 ± 21 | 254 ± 20 |
| Ht (L/L) | 0.50-0.70 | 0.36 ± 0.02 | NR | 0.64 ± 0.01 | 0.57 ± 0.02 |
| Volume Red Blood Cells (mL) | — | 179 ± 12 | NR | 168 ± 16 | 144 ± 15 |
| Hb (g/unit) | min 40 (90% unit) | 61 ± 5.4 | NR | 59 ± 6.5 | 51 ± 6.5 |
| Red Cells | — | 2.05 ± 0.20 | NR | 2.01 ± 0.24 | 1.72 ± 0.21 |

TABLE 5-continued

| Parameter | EP QC criteria | Whole Blood | Before Erythro-Sol3 | After Erythro-Sol3 | Leuko-reduce RCC |
|---|---|---|---|---|---|
| (×10$^{12}$/U) Leukocytes (×10$^9$/U) | <1 × 10$^6$/unit by count (90% of the units tested) | 2.63 ± 0.80 | NR | 2.54 ± 0.11 | 0.09 ± 0.11 |
| Platelets (×10$^9$/U) | — | 78.7 ± 19.8 | NR | 8.88 ± 4.38 | 1.7 ± 0.5 |

It has been suggested that samples having an ATP level greater than 2.7 μmol/g Hb and less than 0.2% hemolysis will have an 80% probability of meeting a limit of 75% of the red blood cells surviving 24 hr after transfusion. (Heaton, W. A. L, Evaluation of posttransfusion recovery and survival of transfused red cells. Transf. Med. Rev. 1992, 6:153-169.) As seen in Table 6 and FIG. 6, the ATP levels in red blood cells prepared from whole blood held from 21 to 23 hours before processing and stored in an E-Sol solution such as E-Sol 3 are above 2.7 μmol/g Hb even after 35 days of storage with hemolysis is at 0.2%. In addition, hemolysis of the red blood cells stored in E-Sol3 also remained below the EU required limit (<0.8%) even on day 56 of storage.

It will be appreciated that weighing components or otherwise expressing the concentrations of components, some experimental variability is expected. The present invention employs the terms "about" or "approximately" to reflect this variability. This variability is typically plus or minus 5% and usually less than 10%.

It will be understood that the embodiments described above are illustrative of some of the applications of the principles of the present subject matter. Numerous modifications may be made by those skilled in the art without departing from the spirit and scope of the claimed subject matter, including those combinations of features that are individually

TABLE 6

| | Day 1 | Day 14 | Day 35 | Day 42 | Day 56 | Requirements (a-b) |
|---|---|---|---|---|---|---|
| Volume, mL | 254 ± 20 | 243 ± 19 | 230 ± 19 | 225 ± 19 | 216 ± 19 | — |
| Ht (%) | 0.57 ± 0.02 | 0.56 ± 0.02 | 0.54 ± 0.02 | 0.55 ± 0.02 | 0.56 ± 0.03 | (a) 0.50-0.70 |
| Hb, g | 51 ± 6.5 | 49 ± 6.0 | 46 ± 5.7 | 44 ± 5.8 | 43 ± 5.9 | (a) Min 40 (90% unit) |
| Hemolysis (%) | 0.04 ± 0.02 | 0.18 ± 0.05 | 0.20 ± 0.04 | 0.25 ± 0.08 | 0.52 ± 0.38 | (a) <0.8% |
| ATP, μmol/g Hb | 5.71 ± 0.60 | 5.37 ± 0.57 | 3.23 ± 0.43 | 2.71 ± 0.39 | 1.47 ± 0.26 | (b) >2.7 μmol/g Hb |
| 2,3 DPG, μmol/g Hb | 3.50 ± 1.0 | 1.04 ± 0.7 | 0.12 ± 0.11 | Below detection limit | Below detection limit | — |
| Glucose, mmol/L | 31.8 ± 2.3 | 24.8 ± 1.8 | 18.4 ± 2.3 | 16.5 ± 2.3 | 14.5 ± 2.6 | — |

(a) EU Standard, 13th edition of Council of Europe

EXAMPLE 3

Red blood cell storage solutions according to the disclosure were also assessed using red blood cells separated from whole blood with an automated red blood cell collection system (Alyx, Fenwal, Inc.). In this case, the whole blood was not held before separation into blood components. Also, the ACD-A (acid, citrate, dextrose) anticoagulant was used instead of CPD. Separated red blood cells were stored with either E-Sol 2, E-Sol 3, E-Sol 4 or SAG-M for up to 42 days and various cellular parameters assessed using methods described previously.

Figure 12:
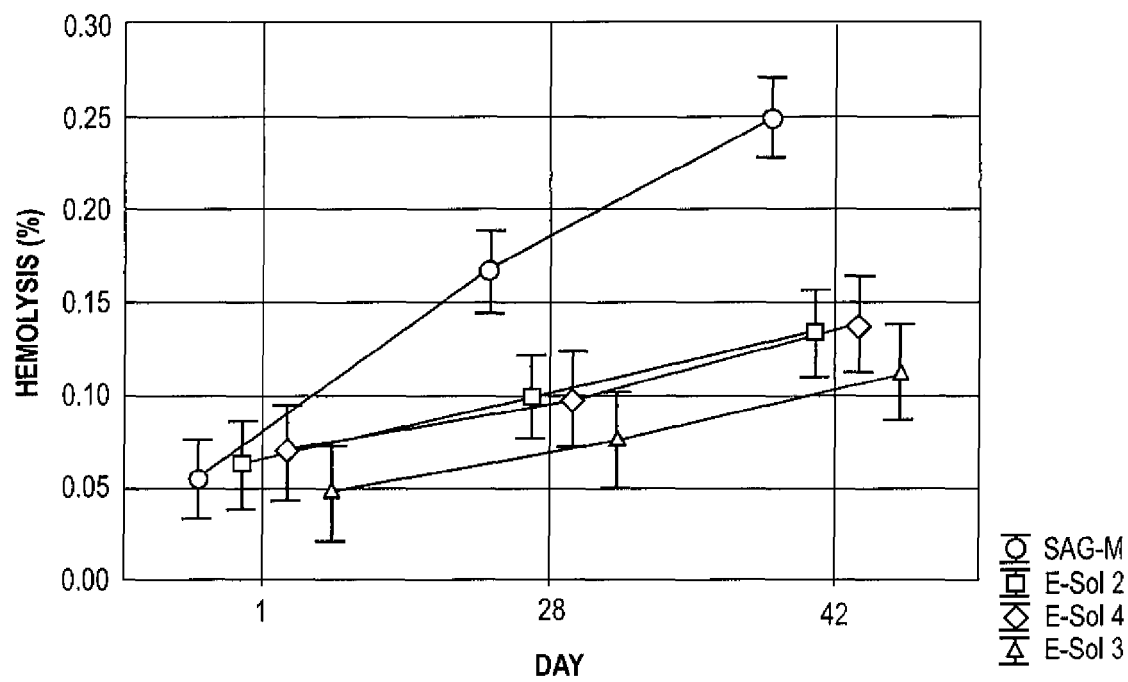
FIG. 12 illustrates graphically levels of hemolysis for red blood cell preparations stored in an aqueous solution described herein.

As shown in FIG. 12, red blood cells separated with an automatic collection system and then stored in either E-Sol 2, E-Sol 3 or E-Sol 4 showed statistically significant lower hemolysis throughout from about day 5 of the storage period compared to cells stored in SAG-M. As degree of hemolysis is generally considered as the single best indicator of cell function, these results indicate that the E-Sol solutions discussed herein (e.g., E-Sol 2, E-Sol 3 and E-Sol 4) are blood storage solutions capable of providing improved red cell functionality when compared to other known storage solutions.

disclosed or claimed herein. For these reasons, the scope hereof is not limited to the above description.

We claim:

1. A synthetic aqueous solution for the storage of red blood cells that have been separated from whole blood wherein said synthetic aqueous solution consists of adenine, mannitol, sodium citrate, sodium phosphate dibasic, and glucose in concentrations of:
   1 mM to 2.2 mM adenine;
   20 mM to 110 mM mannitol;
   2.2 mM to 90 mM sodium citrate;
   16 mM to 30 mM sodium phosphate dibasic; and
   20 mM to 70 mM glucose,
   wherein the pH of the synthetic aqueous solution is between 8.0 and 9.0.

2. The synthetic aqueous solution of claim 1, wherein the volume of the solution is approximately 100-110 ml.

3. The synthetic aqueous solution of claim 1, wherein said adenine, mannitol, sodium citrate, sodium phosphate dibasic, and glucose are present in concentrations of 2.0 mM±less than 10% adenine; 50 mM±less than 10% mannitol; 31.2 mM±less than 10% sodium citrate; 25.0 mM ±less than 10% sodium phosphate dibasic; and 56.8 mM±less than 10% glucose.

4. The synthetic aqueous solution of claim 1, wherein said adenine, mannitol, sodium citrate, sodium phosphate dibasic, and glucose are present in concentrations of 1.9 mM±less than 10% adenine; 45.4 mM±less than 10% mannitol; 28.4 mM±less than 10% sodium citrate; 22.7 mM ±less than 10% sodium phosphate dibasic; and 51.6 mM±less than 10% glucose.

5. A synthetic aqueous solution of for the storage of red blood cells that have been separated from whole blood consisting of adenine, mannitol, sodium citrate, sodium phosphate dibasic, glucose and at least one of acetate and guanosine in concentrations of:
   10 mM to 100 mM acetate ion; and
   0.1 mM to 2.0 mM guanosine;
   1 mM to 2.2 mM adenine;
   20 mM to 110 mM mannitol;
   2.2 mM to 90 mM sodium citrate;
   16 mM to 30 mM sodium phosphate dibasic; and
   20 mM to 70 mM glucose,
   wherein the pH of the synthetic aqueous solution is between 8.0 and 9.0.

6. A synthetic aqueous solution for the storage of red blood cells that have been separated from whole blood consisting of adenine, mannitol, sodium citrate, sodium phosphate dibasic and glucose in concentrations of:
   1 mM to 2.5 mM adenine;
   20 mM to 110 mM mannitol;
   3 mM to 90 mM sodium citrate;
   15 mM to 40 mM sodium phosphate dibasic; and
   20 mM to 140 mM glucose,
   wherein the pH of the synthetic aqueous solution is between 8.0 and 9.0.

7. The synthetic aqueous solution of claim 6, wherein the volume of the synthetic aqueous solution is approximately 100-110 ml.

8. The synthetic aqueous solution of claim 6, wherein the volume of the synthetic aqueous solution is approximately 105 ml.

9. A synthetic aqueous solution for the storage of red blood cells that have been separated from whole blood consisting of adenine, mannitol, sodium citrate, sodium phosphate dibasic, glucose and at least one of acetate ion and guanosine in the concentrations of:
   1 mM to 2.5 mM adenine;
   20 mM to 110 mM mannitol;
   3 mM to 90 mM sodium citrate;
   15 mM to 40 mM sodium phosphate dibasic; and
   20 mM to 140 mM glucose,
   wherein the pH of the synthetic aqueous solution is between 8.0 and 9.0; further 10 mM to 100 mM acetate ion; and 0.1 mM to 2.0 mM guanosine.

10. A method for storing red blood cells comprising the steps of:
    providing a unit of anticoagulated whole blood,
    holding the whole blood from about four hours to about twenty-six hours;
    separating the red blood cells from the whole blood; and
    adding to the separated red blood cells the aqueous synthetic solution of claim 5, 6, or 9.

11. The method of claim 10 comprising adding from about 90 ml to 120 ml of said aqueous storage solution to said red blood cells.

12. The method of claim 11 comprising adding from about 100 ml to 110 ml of said aqueous storage solution to said red blood cells.

13. The method of claim 10 wherein the concentration of said sodium phosphate dibasic is from about 22 mM±less than 10% to 28 mM±less than 10%.

14. The method of claim 10 wherein said aqueous storage solution comprises: 2.0 mM adenine±less than 10%; 50 mM mannitol±less than 10%; 31.2 mM sodium citrate±less than 10%; 25.0 mM sodium phosphate dibasic±less than 10%; and 56.8 mM glucose±less than 10%.

15. The method of claim 10 wherein said aqueous storage solution comprises: 1.9 mM adenine±less than 10%; 45.4 mM mannitol±less than 10%; 28.4 mM sodium citrate±less than 10%; 22.7 mM sodium phosphate dibasic±less than 10%; and 51.6 mM glucose±less than 10%.

16. The method of claim 10 wherein the pH of the aqueous storage solution is from 8.3±less than 5% to 8.5±less than 5%.

17. The method of claim 10 further comprising storing said red blood cells in said aqueous solution for at least 35 days wherein said red blood cells retain cell functionality during said storing as measured by degree of hemolysis.

18. The method of claim 10 further comprising storing said red blood cells in said aqueous solution for at least 35 days wherein said red blood cells retain cell functionality during said storing as measured by retention of at least 50% of initial ATP in said red blood cells.

* * * * *